US012605410B2

(12) United States Patent (10) Patent No.: US 12,605,410 B2
Yivgi-Ohana et al. (45) Date of Patent: Apr. 21, 2026

(54) MITOCHONDRIA-ENRICHED GENETICALLY ENGINEERED CELLS AND USES THEREOF

(71) Applicants: Minovia Therapeutics Ltd., Tirat Hacarmel (IL); Tel Hashomer Medical Research Infrastructure and Services Ltd., Ramat Gan (IL)

(72) Inventors: Natalie Yivgi-Ohana, Haifa (IL); Noa Sher, Haifa (IL); Moriya Blumkin, Tel Aviv (IL); Elad Jacoby, Ramat Gan (IL)

(73) Assignees: Minovia Therapeutics Ltd., Tirat Hacarmel (IL); Tel Hashomer Medical Research Infrastructure and Services Ltd., Ramat Gan (IL)

( * ) Notice: Subject to any disclaimer, the term of this patent is extended or adjusted under 35 U.S.C. 154(b) by 896 days.

(21) Appl. No.: 17/910,304

(22) PCT Filed: Mar. 30, 2021

(86) PCT No.: PCT/IL2021/050358
§ 371 (c)(1),
(2) Date: Sep. 8, 2022

(87) PCT Pub. No.: WO2021/199040
PCT Pub. Date: Oct. 7, 2021

(65) Prior Publication Data
US 2023/0123731 A1 Apr. 20, 2023

Related U.S. Application Data

(60) Provisional application No. 63/003,184, filed on Mar. 31, 2020.

(51) Int. Cl.
*A61K 35/545* (2015.01)
*A61K 38/17* (2006.01)
(Continued)

(52) U.S. Cl.
CPC ........ *A61K 35/545* (2013.01); *A61K 38/1774* (2013.01); *A61K 40/11* (2025.01);
(Continued)

(58) Field of Classification Search
CPC .. A61K 35/545; A61K 38/1774; A61K 40/11; A61K 40/31; A61K 40/4211;
(Continued)

(56) References Cited

U.S. PATENT DOCUMENTS 6,590,141 B1 7/2003 Frohberg
6,616,926 B1 9/2003 Burkly et al.
(Continued)

FOREIGN PATENT DOCUMENTS

AU 2012201710 B2 1/2014
CN 102266350 A 12/2011
(Continued)

OTHER PUBLICATIONS

Harris, Daniel T, and David M Kranz. "Adoptive T Cell Therapies: A Comparison of T Cell Receptors and Chimeric Antigen Receptors." Trends in pharmacological sciences vol. 37,3 (2016): 220-230. (Year: 2016).*

(Continued)

*Primary Examiner* — Tracy Vivlemore
*Assistant Examiner* — Thomas R. Amick
(74) *Attorney, Agent, or Firm* — The Roy Gross Law Firm, LLC; Roy D. Gross

(57) ABSTRACT

The present invention is based on the discovery that cells enriched with mitochondria are useful for treating diseases and disorders. Disclosed are pharmaceutical compositions of mitochondrially-enriched genetically engineered T cells and methods of treatment using mitochondrially-enriched genetically engineered T cells.

18 Claims, 4 Drawing Sheets

Mitochondrially enriched CAR-T cells: Day 5

ATP content

Citrate Synthase Activity

% Viability

(51) Int. Cl.

| | |
|---|---|
| *A61K 40/11* | (2025.01) |
| *A61K 40/31* | (2025.01) |
| *A61K 40/42* | (2025.01) |
| *C12N 5/0783* | (2010.01) |
| *C12N 15/86* | (2006.01) |

(52) U.S. Cl.

CPC .......... *A61K 40/31* (2025.01); *A61K 40/4211* (2025.01); *C12N 5/0636* (2013.01); *C12N 15/86* (2013.01); *C12N 2502/025* (2013.01); *C12N 2740/10043* (2013.01)

(58) Field of Classification Search

CPC .................... A61K 35/28; A61K 35/17; A61K 2039/5156; A61K 39/0011; C12N 5/0636; C12N 15/86; C12N 2502/025; C12N 2740/10043; C12N 2510/00; A61P 35/00; C07K 14/7051

See application file for complete search history.

(56) References Cited

U.S. PATENT DOCUMENTS

| | | | |
|---|---|---|---|
| 6,929,806 | B2 | 8/2005 | Toba et al. |
| 7,238,727 | B2 | 7/2007 | Satomi et al. |
| 7,279,326 | B2 | 10/2007 | Weissig et al. |
| 7,339,090 | B2 | 3/2008 | Christmann |
| 7,407,800 | B1 | 8/2008 | Benton et al. |
| 9,603,872 | B2 | 3/2017 | Cataldo et al. |
| 10,213,459 | B2 | 2/2019 | Yivgi-Ohana et al. |
| 10,738,278 | B2 | 8/2020 | Mohler et al. |
| 2001/0021526 | A1 | 9/2001 | Davis et al. |
| 2003/0113389 | A1 | 6/2003 | Wang et al. |
| 2004/0122109 | A1 | 6/2004 | Fujii et al. |
| 2004/0192627 | A1 | 9/2004 | Weissig et al. |
| 2005/0153381 | A1 | 7/2005 | Marusich et al. |
| 2005/0164933 | A1 | 7/2005 | Tymianski et al. |
| 2006/0024277 | A1 | 2/2006 | Sivak et al. |
| 2006/0241034 | A1 | 10/2006 | Chauvier et al. |
| 2008/0057039 | A1 | 3/2008 | Newell Rogers et al. |
| 2010/0278790 | A1 | 11/2010 | Prockop et al. |
| 2011/0008310 | A1 | 1/2011 | Cataldo et al. |
| 2011/0105359 | A1 | 5/2011 | Czerwinski |
| 2012/0058091 | A1 | 3/2012 | Rogers et al. |
| 2012/0107285 | A1 | 5/2012 | Hyde et al. |
| 2012/0107937 | A1 | 5/2012 | Hyde et al. |
| 2013/0022666 | A1 | 1/2013 | Brzezinska |
| 2013/0034527 | A1 | 2/2013 | Hyde et al. |
| 2013/0149778 | A1 | 6/2013 | Chang et al. |
| 2014/0193511 | A1 | 7/2014 | Yivgi-Ohana et al. |
| 2015/0045403 | A1 | 2/2015 | Shanler et al. |
| 2015/0079193 | A1 | 3/2015 | Yivgi-Ohana et al. |
| 2015/0313950 | A1 | 11/2015 | Gammelsaeter et al. |
| 2015/0344844 | A1 | 12/2015 | Better et al. |
| 2015/0374736 | A1 | 12/2015 | Lee |
| 2015/0374756 | A1 | 12/2015 | Frank et al. |
| 2016/0346333 | A1 | 12/2016 | Hariri |
| 2017/0015287 | A1 | 1/2017 | Sander et al. |
| 2017/0065635 | A1 | 3/2017 | Cataldo et al. |
| 2017/0080030 | A1 | 3/2017 | Peirce-Cottler et al. |
| 2017/0151287 | A1 | 6/2017 | von Maltzahn et al. |
| 2017/0204372 | A1 | 7/2017 | Mohler et al. |
| 2018/0007913 | A1 | 1/2018 | Sceats et al. |
| 2018/0030413 | A1 | 2/2018 | Yivgi-Ohana et al. |
| 2020/0009198 | A1 | 1/2020 | Choi et al. |
| 2020/0054682 | A1* | 2/2020 | Gojo .................... C12N 5/0647 |
| 2020/0239850 | A1 | 7/2020 | Yivgi-Ohana et al. |
| 2020/0246379 | A1 | 8/2020 | Yivgi-Ohana et al. |
| 2020/0377951 | A1 | 12/2020 | Bettoun |
| 2021/0260137 | A1 | 8/2021 | Yivgi Ohana et al. |
| 2023/0338427 | A1 | 10/2023 | Yivgi-Ohana et al. |

FOREIGN PATENT DOCUMENTS

| | | | |
|---|---|---|---|
| CN | 102293178 | A | 12/2011 |
| CN | 103976935 | A | 8/2014 |
| CN | 106795490 | A | 5/2017 |
| DE | 102013225588 | A1 | 4/2014 |
| GB | 2350565 | A | 12/2000 |
| JP | 2002523434 | A | 7/2002 |
| JP | 2004500409 | A | 1/2004 |
| JP | 2006131600 | A | 5/2006 |
| JP | 2008545779 | A | 12/2008 |
| JP | 2014501764 | A | 1/2014 |
| JP | 2018507690 | A | 3/2018 |
| WO | WO 2003/014317 | A2 | 2/2003 |
| WO | WO 2004100773 | A2 | 11/2004 |
| WO | WO 2008000001 | A1 | 1/2008 |
| WO | WO 2008137035 | A1 | 11/2008 |
| WO | WO 2008152640 | A2 | 12/2008 |
| WO | WO 2011059547 | A2 | 5/2011 |
| WO | WO 2013002880 | A1 | 1/2013 |
| WO | WO 2013035101 | A1 | 3/2013 |
| WO | WO 2013/082243 | A1 | 6/2013 |
| WO | WO 2013171752 | A1 | 11/2013 |
| WO | WO 2014/130518 | A1 | 8/2014 |
| WO | WO 2016008937 | A1 | 1/2016 |
| WO | WO 2016049867 | A1 | 4/2016 |
| WO | WO 2016/076434 | A1 | 5/2016 |
| WO | WO 2016113544 | A1 | 7/2016 |
| WO | WO 2016135723 | A1 | 9/2016 |
| WO | WO 2016138420 | A1 | 9/2016 |
| WO | WO 2017124037 | A1 | 7/2017 |
| WO | WO 2018083700 | A1 | 5/2018 |
| WO | WO 2018088874 | A1 | 5/2018 |
| WO | WO 2018101708 | A1 | 6/2018 |
| WO | WO 2018178970 | A1 | 10/2018 |
| WO | WO 2020021535 | A1 | 1/2020 |
| WO | WO 2020021536 | A1 | 1/2020 |
| WO | WO 2020021537 | A1 | 1/2020 |
| WO | WO 2020021538 | A1 | 1/2020 |
| WO | WO 2020021539 | A1 | 1/2020 |
| WO | WO 2020021541 | A1 | 1/2020 |
| WO | WO 2020/036973 | A1 | 2/2020 |
| WO | WO 2020021540 | A9 | 4/2020 |
| WO | WO 2020021541 | A9 | 2/2021 |
| WO | WO 2021199040 | A1 | 10/2021 |

OTHER PUBLICATIONS

Dasyam (Dasyam, Nathaniel, Philip George, and Robert Weinkove. "Chimeric antigen receptor T-cell therapies: Optimising the dose." British journal of clinical pharmacology 86.9 (2020): 1678-1689). (Year: 2020).*

Rosa et al., "Vitamin C and E supplementation prevents mitochondrial damage of ileum myocytes caused by intense and exhaustive exercise training", J Appl Physiol, Aug. 2009, 107: 1532-1538.

Sookoian et al., "Mitochondrial genome architecture in non-alcoholic fatty liver disease", Journal of Pathology, Oct. 2016, 240: 437-449.

Tomizawa et al., "Elevated levels of alanine transaminase and triglycerides within normal limits are associated with fatty liver", Experimental and Therapeutic Medicine, May 8, 2014: 759-762.

De Maranon et al., "Targeting mitochondria: a great boon to type 2 diabetes", Redox Experimental Medicine, Aug. 2022, 2022(1): R127-138.

Garone et al., "Clinical and genetic spectrum of mitochondrial neurgastrointestinal encephalomyopathy", Brain, 2011, 134: 3326-3332.

JP Office Action in Japanese Application No. 2021-503582, dated Feb. 19, 2024, 13 pages (with English translation).

Nishigaki et al., "Mitochondrial Dysfunctions and Age-associated Diseases", Japanese Journal of Geriatrics, 2006, 43(3): 274-282, 15 pages (with English abstract).

Seo et al., "Age-related changes in skeletal muscle mitochondria: the role of exercise", Integrative Medicine Research, Jul. 2016, 5(3): 182-186.

(56) References Cited

OTHER PUBLICATIONS

Wakino et al., "The Cutting-Edge or Medicine: Aging and Chronic Kidney Disease", Japanese Journal of Geriatrics, 2017, 106(5): 1019-1028, 12 pages (with English abstract).

EP Office Action in European application No. 19840282.8, dated Jan. 9, 2024, 13 pages.

Gollihue et al., "Prospects for therapeutic mitochondrial transplantation", Mitochondrion, 2017, 35: 70-79.

Lodi et al., "Deficit of in vivo mitochondrial ATP production in patients with Friedreich ataxia", Proc. Natl. Acad. Sci, Sep. 1999, 96: 11492-11495.

Ahmed et al., "Human Epidermal Growth Factor Receptor 2 (HER2)-Specific Chimeric Antigen Receprot Modified T Cells for the Immunotherapy of HER2 positive Sarcoma", Journal of Clinical Oncology, May 2015 vol. 33, No. 15 pp. 1688-1696. doi: 10.1200/JCO.2014.58.0225. Epub Mar. 23, 2015. PMID: 25800760; PMCID: PMC4429176.

Bartelink, Imke H., et al., "Association between busulfan exposure and outcome in children receiving intravenous busulfan before hematologic stem cell transplantation" Biology of blood and marrow transplantation 15.2 (2009) 231-241. DOI:10.1016/j.bbmt.2008.11.022.

Caldas de Andrade et al., "Bone marrow mononuclear cell transplantation improves mitochondrial bioenergetics in the liver of cholestatic rats" Experimental Cell Research, vol. 336, Issue 1, 2015, pp. 15-22, doi: 10.1016/j.yexcr.2015.05.002. Epub May 12, 2015. PMID: 25978973.

Canadian Center Society, 2024, "Side effects of a stem cell transplant". Available online: [https://cancer.ca/en/treatments/treatment-types/stem-cell-transplant/side-effects-of-stem-cell-transplant], 10pp.

Cherry, AB et al., "Induced Pluripotent Stem Cells with a Mitochondrial DNA Deletion", Stem Cells 2013;31:1287-1297, doi: 10.1002/stem.1354. PMID: 23400930; PMCID: PMC3692613.

Greiff, D., and M. Myers. "Effect of dimethyl sulphoxide on the cryo-tolerance of mitochondria." Nature 190.4782 (1961): 1202-1204. https://doi.org/10.1038/1901202b0.

Imamura Yoji et al., "Angiogenic therapy using autologous bone marrow stem cells: Results of autologous bone marrow cells implantation (BMI) for hindlimb and ischemic myocardium", Journal of Saitama Medical University, 2003, vol. 30, No. 4, p. 195, 2pp.

Masakaba Tagawa et al., "Cell therapy using bone marrow mononuclear cells" J Jpn Coll Angiol, 2006, vol. 46, pp. 281-288, 18pp.

Mi Jin Kim et al., "Delivery of Exogenous mitochondria via centrifugation enhances cellular metabolic function" Scientific Reports, vol. 8, No. 1, 3330, Feb. 20, 2018, 13pp. https://doi.org/10.1038/s41598-018-21539-y.

Naing et al., "Maternally inherited diabetes and deafness (MIDD): Diagnosis and management", Journal of Diabetes and its Complications, vol. 28, Issue 4, 2014, pp. 542-546, doi: 10.1016/j.jdiacomp.2014.03.006. Epub Mar. 12, 2014. PMID: 24746802.

Niyazov et al., "Primary mitochondrial disease and secondary mitochondrial dysfuntion: importance of distinction for diagnosis and treatment", molecular syndromology, Jul. 2016: 122-137, doi: 10.1159/000446586. Epub Jun. 3, 2016. PMID: 27587988; PMCID: PMC4988248.

Nukala, Vidya N., et al. "Cryopreservation of brain mitochondria: a novel methodology for functional studies", Journal of neuroscience methods 152.1-2 (2006): 48-54. doi: 10.1016/j.jneumeth.2005.08.017. Epub Oct. 24, 2005. PMID: 16246427.

Prasun P, Ginevic I, Oishi K. "Mitochondrial dysfunction in non-alcoholic fatty liver disease and alcohol related liver disease". Transl Gastroenterol Hepatol. Jan. 5, 2021;6:4. doi: 10.21037/tgh-20-125. PMID: 33437892; PMCID: PMC7792990.

Rao et al., "The proteome of higher plant mitochondria". Mitochondrion, Mar. 2017;33:22-37. doi: 10.1016/j.mito.2016.07.002. Epub Jul. 9, 2016. PMID: 27405097.

Rotig et al., "Spectrum of mitochondrial DNA rearrangements in the Pearson marrow-pancreas syndrome.", Human molecular genetics, 1995, 4(8): 1327-1330, doi: 10.1093/hmg/4.8.1327. PMID: 7581370.

Rovira-Llopis et al.,, "Mitochondrial dynamics in type 2 diabetes: Pathophysiological implications", Redox Biology, vol. 11, 2017, pp. 637-645, doi: 10.1016/j.redox.2017.01.013. Epub Jan. 16, 2017. PMID: 28131082; PMCID: PMC5284490.

Silva, Gisele S. et al., "Causes of ischemic stroke". In Acute ischemic stroke: Imaging and intervention (2nd edition)n R. Gilberto González et al (Eds.), Springer-Verlag Berlin Heidelberg 2011, pp. 25-42. DOI: 10.1007/978-3-642-12751-9_2.

Wang et al., "Stem cell-derived mitochondria transplantation: A Novel strategy and the challenges for the treatment of tissue injury", stem cell research & therapy, 2018 9(106), 10 pages, doi: 10.1186/s13287-018-0832-2. PMID: 29653590; PMCID: PMC5899391.

Weihong Yan et al."Umbilical Cord MSCs Reverse D-Galactose-Induced Hepatic Mitochondrial Dysfunction via Activation of Nrf2/HO-1 Pathway", Biological and Pharmaceutical Bulletin, Aug. 1, 2017;40(8): 1174-1182. doi: 10.1248/bpb.b16-00777. Epub May 13, 2017. PMID: 28502921.

Yu-Wai-Man, P. Griffiths et al. "2009 Inherited mitochondrial optic neuropathies". Journal of medical genetics, 46(3), pp. 145-158 (2008). doi: 10.1136/jmg.2007.054270. Epub Nov. 10, 2008. Erratum in: J Med Genet. Apr. 2011;48(4):284. PMID: 19001017; PMCID: PMC2643051.

Zhan et al., "Mitochondrial Dynamics: Regulatory mechanisms and Emerging role in renal pathophysiology", Kidney International, 2013, 83(4): 568-581. doi: 10.1038/ki.2012.441. Epub Jan. 16, 2013. PMID: 23325082; PMCID: PMC3612360.

Augustyniak et al., "Mitochondrial Biogenesis and Neural Differentiation of Human iPSC is Modulated by Idebenone in a Developmental Stage-Dependent Manner," Biogerontology, 2017, 18: 665-677.

CN Office Action in Chinese Application No. 201980054078.2, dated Oct. 27, 2023, 20 pages (with English translation).

Shi et al., "Intravenous Administration of Mitochondria for Treating Experimental Parkinson's Disease," Mitochondrion, May 2017, 34: 91-100.

Abramova N.B., et al., "Injection of Mitochondria Into Oocytes and Fertilized Eggs," Ontogenez, 1979, vol. 10, No. 4, pp. 401-405 (Translated abstract), 1 Page.

Abramova N.B., et al., "Regulation of the Number and Function of Mitochondria During Artificial Increase of their Mass in Fish Embryos," Biokhimiia, PMID: 6626595, Aug. 1983, vol. 48, No. 8, 1 Page, (Translated Abstract).

Abramova N.B., et al., "The Functioning of Mammalian Mitochondria Injected Into Fish Embryos," Ontogenez, PMID: 2549481, vol. 20, No. 3, May-Jun. 1989, 1 Page, (Translated Abstract).

Alaynick W.A., et al., "Nuclear Receptors, Mitochondria And Lipid Metabolism," Mitochondrion, Sep. 30, 2008, vol. 8, No. 4, pp. 329-337, 17 Pages, DOI: 10.1016/j.mito.2008.02.001, XP025474006.

Anonymous: "History of Changes for Study: NCT03384420," Dec. 24, 2017, 4 Pages, XP055876311, [Retrieved on Jan. 5, 2022] Retrieved From URL: https://clinicaltrials.gov/ct2/history/NCT03384420?V_1=View#StudyPageTop.

Anonymous, "William's Blog | The Champ Foundation," Conference Recap, Feb. 15, 2018, 5Pages, XP055876318, [Retrieved on Jan. 5, 2022] Retrieved from URL:https://www.thechampfoundation.org/williams-story.html?entry=32.

Au K.M., et al., "Mitochondrial DNA Deletion in a Girl with Fanconi's Syndrome," Pediatric Nephrology, Sep. 12, 2007, vol. 22, pp. 136-140.

Babenko V.A., "Mirol Enhances Mitochondria Transfer from Multipotent Mesenchymal Stem Cells (MMSC)to Neural Cells and Improves the Efficacy of Cell Recovery," Molecules, Mar. 19, 2018, vol. 23, No. 3, 14 pages.

Baker et al., "Use of the Mouse Aortic Ring Assay to Study Angiogenesis," 2012, Nature Protocols 7(1): 89-104.

Biolog, "MitoPlate™ S-1 and MitoPlate™ I-1 for Characterization of Mammalian Cell Mitochondria," 2020, pp. 1-12.

Bourgeron T., et al., "Isolation And Characterization of Mitochondria From Human B Lymphoblastoid Cell Lines," Biochemical and Biophysical Research Communications, Jul. 15, 1992, vol. 186, No. 1, pp. 16-23, XP055144685.

(56) References Cited

OTHER PUBLICATIONS

Brass et al., "Multiple Skeletal Muscle Mitochondrial DNA Deletions in Patients with Unilateral Peripheral Arterial Disease," 2000, Vascular Medicine 5(4):225-230.

Caicedo A., et al., "Mitoception as a New Tool to Assess the Effects of Mesenchymal Stem/Stromal Cell Mitochondria on Cancer Cell Metabolism and Function," Scientific Reports, Mar. 13, 2015, vol. 5, No. 1, Article 9073, pp. 1-10.

Cardenes N., et al., "De Mesenchymal Stem Cells: a Promising Therapy for the Acute Respiratory Distress Syndrome," Respiration, Feb. 2013, vol. 85, No. 4, pp. 267-278.

Chan D.C., et al., "Mitochondrial Fusion and Fission in Mammals," Annual Review of Cell and Developmental Biology, 2006, vol. 22, pp. 79-99.

Che R., et al., "Mitochondrial Dysfunction in the Pathophysiology of Renal Diseases," American Journal of Physiology—Renal Physiology, 2014, vol. 306, pp. F367-F378.

Chemicon International Inc.: "Adipogenesis Assay Kit," Cat. No. ECM950, 2004, Revision C, 41448, 12 Pages.

Chen et al. "Inhibition of Triglyceride Synthesis as a Treatment Strategy for Obesity: Lessons From DGAT1-Deficient Mice" 2005, Arteriosclerosis, Thrombosis and Vascular Biology 25(3):482-486.

Chen M., et al., "Generation of Retinal Ganglion-like Cells From Reprogrammed Mouse Fibroblasts," Investigative Ophthalmology & Visual Science, 2010, vol. 51, No. 11, pp. 5970-5978.

Chinnery P.F., et al., "The Challenges of Mitochondrial Replacement," PLoS Genetics, Published on Apr. 24, 2014, vol. 10, No. 4, e1004315, 2 Pages.

Choi Y-S., et al., "Analysis of Proteome Bound To D-loop Region of Mitochondrial DNA By DNA-linked Affinity Chromatography And Reverse-Phase Liquid Chromatography/Tandem Mass Spectrometry," Annals of the New York Academy of Sciences, May 31, 2005, vol. 1042, pp. 88-100, XP055035180.

Clark M.A., et al., "Mitochondrial Transformation of Mammalian Cells," Nature, Macmillan Journals Ltd, London, GB, Feb. 18, 1982, vol. 295, No. 5850, pp. 605-607, ISSN 0028-0836, XP002625375.

Cook G.A., et al., "Structural Changes of Isolated Hepatocytes During Treatment With Digitonin," Biochimica et Biophysica Acta (BBA)—Molecular Cell Research, Dec. 1983, vol. 763, No. 4, pp. 356-367.

Corcelli A., et al., "Mitochondria Isolated in Nearly Isotonic Kci Buffer: Focus on Cardiolipin and Organelle Morphology," Biochimica et Biophysica Acta 1798, 2010, pp. 681-687.

Cowdry N.H., "A Comparison of Mitochondria in Plant and Animal Cells," The Biological Bulletin, 1917, vol. 33, No. 3, pp. 196-228.

Csordas A., "Mitochondrial Transfer Between Eukaryotic Animal Cells And Its Physiologic Role," Rejuvenation Research, Feb. 2006, vol. 9, No. 4, pp. 450-454.

Das Neves R.P., et al., Connecting Variability in Global Transcription Rate to Mitochondrial Variability, PLoS biology, 2010, vol. 8, No. 12, e1000560.

English Translation of Notice of Reasons for Rejection for Japanese Application No. 2021-142214, dated Jun. 21, 2022, 15 Pages.

Extended European Search Report for European Application No. 12830575.2, mailed Feb. 13, 2015, 11 Pages.

Extended European Search Report for European Application No. 16754857.7, mailed Jul. 13, 2018, 06 Pages.

Extended European Search Report for European Application No. 18774886.8, mailed Oct. 26, 2020, 7 Pages.

Extended European Search Report for European Application No. 19776644.7, mailed Jul. 12, 2021, 06 Pages.

Extended European Search Report for European Application No. 19840137.4, mailed Apr. 22, 2022, 9 Pages.

Extended European Search Report for European Application No. 19840282.8, mailed Apr. 22, 2022, 7 Pages.

Extended European Search Report for European Application No. 19840685.2, mailed Apr. 22, 2022, 9 Pages.

Extended European Search Report for European Application No. 19840774.4, mailed May 6, 2022, 8 Pages.

Extended European Search Report for European Application No. 19841283.5, mailed May 6, 2022, 8 Pages.

Extended European Search Report for European Application No. 19841655.4, mailed Mar. 11, 2022, 17 Pages.

Extended European Search Report for European Application No. 19841817.0, mailed May 6, 2022, 7 Pages.

Extended European Search Report for European Application No. 19842284.2, mailed May 4, 2022, 8 Pages.

Finsterer J., et al., "Renal Manifestations of Primary Mitochondrial Disorders," Biomedical Reports May 2014 Spandidos Publications GBR, vol. 6, No. 5, May 1, 2017, pp. 487-494.

Frazier A.E., et al., "Mitochondrial Morphology and Distribution in Mammalian Cells," Journal of Biological Chemistry, Dec. 2006, vol. 387, No. 12, 9 Pages.

Frezza C., et al., "Organelle Isolation: Functional Mitochondria From Mouse Liver, Muscle And Cultured Fibroblasts," Nature Protocols, Feb. 22, 2007, vol. 2, No. 2, pp. 287-295, ISSN 1750-2799, XP055038328.

Fu A., et al., "Mitotherapy for Fatty Liver by Intravenous Administration of Exogenous Mitochondria in Male Mice," Frontiers in Pharmacology, Jan. 2017, vol. 8, Article 241, pp. 1-8.

Galipeau J., et al., "Mesenchymal Stromal Cells: Clinical Challenges and Therapeutic Opportunities," Cell Stem Cell, Jun. 1, 2018, vol. 22, pp. 824-839.

Gasnier F., et al., "Use of Percoll Gradients for Isolation of Human Placenta Mitochondria Suitable for Investigating Outer Membrane Proteins," Analytical Biochemistry, Academic Press Inc., New York, Jul. 1, 1993, vol. 212, No. 1, pp. 173-178, doi: 10.1006/ABIO.1993. 1309, ISSN 0003-2697, XP024763625.

Gavazza M., et al., "Sensitivity of Mitochondria Isolated From Liver And Kidney of Rat And Bovine To Lipid Peroxidation: A Comparative Study of Light Emission And Fatty Acid Profiles," Molecular And Cellular Biochemistry, Kluwer Academic Publishers, BO, Dec. 1, 2005, vol. 280, No. 1-2, pp. 77-82, ISSN 1573-4919, XP019288940.

Gollihue J.L., et al., "Mitochondrial Transplantation Strategies as Potential Therapeutics for Central Nervous System Trauma," Neural Regeneration Research, Feb. 1, 2018, vol. 13, No. 2, pp. 194-197, XP055681115.

Govers L.P., et al., "Mitochondrial DNA Mutations in Renal Disease: An Overview," Pediatric Nephrology, Jan. 2021, vol. 36, pp. 9-17.

Gowda S., et al., "Markers of Renal Function Tests," North American Journal of Medical Sciences, Apr. 2010, vol. 2, No. 4, pp. 170-173.

Griffiths E.J., et al., "Mitochondrial Calcium As A Key Regulator of Mitochondrial ATP Production In Mammalian Cells," Biochimica Et Biophysica Acta, Mar. 2009, vol. 1787, No. 11, pp. 1324-1333.

Guantes, et al., "Mitochondria and the Non-Genetic Origins of Cell-to-Cell Variability: More is Different," BioEssays, 2016, vol. 38, No. 1, pp. 64-76.

Hall A.M., et al., "The Not So 'Mighty Chondrion': Emergence of Renal Diseases Due to Mitochondrial Dysfunction," Nephron Physiology, 2007, vol. 105, 10 Pages.

Hartwig S., et al., "A Critical Comparison Between Two Classical And A Kit-based Method For Mitochondria Isolation," Proteomics, Jan. 31, 2009, vol. 9, No. 11, pp. 3209-3214, XP055144705.

Hashimi M., et al., "Nephritic Syndrome," StatPearls [Internet], Treasure Island (FL): StatPearls Publishing, NCBI Bookshelf, A service ofthe National Library of Medicine, National Institutes of Health, Jan. 2021, pp. 1-8.

Hassanein T., "Mitochondrial Dysfunction in Liver Disease and Organ Transplantation," Mitochondrion, vol. 4, Sep. 2004, pp. 609-620.

Hosten A.O., "BUN and Creatinine," Clinical Methods: The History, Physical, and Laboratory Examinations, Chapter 193, 3rd Edition, 1990, pp. 874-878.

International Preliminary Report on Patentability for International Application No. PCT/IL2012/050359, mailed Mar. 20, 2014, 7 Pages.

International Preliminary Report on Patentability for International Application No. PCT/IL2016/050205, mailed Sep. 8, 2017, 10 Pages.

(56) References Cited

OTHER PUBLICATIONS

International Preliminary Report on Patentability for International Application No. PCT/IL2018/050332, mailed Oct. 10, 2019, 8 Pages.
International Preliminary Report on Patentability for International Application No. PCT/IL2019/050350, mailed Oct. 8, 2020, 8 Pages.
International Preliminary Report on Patentability for International Application No. PCT/IL2019/050821, mailed Feb. 4, 2021, 8 Pages.
International Preliminary Report on Patentability for International Application No. PCT/IL2019/050822, mailed Feb. 4, 2021, 8 Pages.
International Preliminary Report on Patentability for International Application No. PCT/IL2019/050823, mailed Feb. 4, 2021, 10 Pages.
International Preliminary Report on Patentability for International Application No. PCT/IL2019/050824, mailed Feb. 4, 2021, 7 Pages.
International Preliminary Report on Patentability for International Application No. PCT/IL2019/050825, mailed Feb. 4, 2021, 10 Pages.
International Preliminary Report on Patentability for International Application No. PCT/IL2019/050826, mailed Feb. 4, 2021, 9 Pages.
International Preliminary Report on Patentability for International Application No. PCT/IL2019/050827, mailed Feb. 4, 2021, 9 Pages.
International Preliminary Report on Patentability for International Application No. PCT/IL2019/050828, mailed Feb. 4, 2021, 8 Pages.
International Preliminary Report on Patentability for International Application No. PCT/IL2021/050349, mailed Oct. 13, 2022, 11 Pages.
International Preliminary Report on Patentability for International Application No. PCT/IL2021/050358, mailed Oct. 13, 2022, 8 Pages.
International Preliminary Report on Patentability for the application No. PCT/IL2022/050098, mailed Jul. 20, 2023, 9 pages.
International Search Report and Written Opinion for Application No. PCT/IL2022/050098, mailed on May 26, 2022, 10 Pages.
International Search Report and Written Opinion for Application No. PCT/IL2022/051280, mailed on Dec. 1, 2022, 13 pages.
International Search Report and Written Opinion for International Application No. PCT/IL2012/050359, mailed Nov. 25, 2012, 10 Pages.
International Search Report and Written Opinion for International Application No. PCT/IL2016/050205, mailed Jun. 19, 2016, 13 Pages.
International Search Report and Written Opinion for International Application No. PCT/IL2018/050332, mailed Jun. 13, 2018, 11 Pages.
International Search Report and Written Opinion for International Application No. PCT/IL2019/050350, mailed Jul. 7, 2019, 10 Pages.
International Search Report and Written Opinion for International Application No. PCT/IL2019/050821, mailed Nov. 26, 2019, 9 Pages.
International Search Report and Written Opinion for International Application No. PCT/IL2019/050822, mailed Nov. 27, 2019, 11 Pages.
International Search Report and Written Opinion for International Application No. PCT/IL2019/050823, mailed Nov. 18, 2019, 11 Pages.
International Search Report and Written Opinion for International Application No. PCT/IL2019/050824, mailed Dec. 15, 2019, 8 Pages.
International Search Report and Written Opinion for International Application No. PCT/IL2019/050825, mailed Nov. 28, 2019, 11 Pages.
International Search Report and Written Opinion for International Application No. PCT/IL2019/050826, mailed Nov. 24, 2019, 10 Pages.
International Search Report and Written Opinion for International Application No. PCT/IL2019/050827, mailed Nov. 20, 2019, 11 Pages.

International Search Report and Written Opinion for International Application No. PCT/IL2019/050828, mailed Nov. 24, 2019, 11 Pages.
International Search Report and Written Opinion for International Application No. PCT/IL2021/050349, mailed Aug. 17, 2021, 14 Pages.
International Search Report and Written Opinion for International Application No. PCT/IL2021/050358, mailed Jul. 20, 2021, 10 Pages.
Islam M.N., et al., "Mitochondrial Transfer From Bone-marrow-derived Stromal Cells to Pulmonary Alveoli Protects Against Acute Lung Injury," Nature Medicine, Apr. 15, 2012, vol. 18, No. 5, pp. 759-765, 15 Pages, XP055475523, Retrieved from URL: http://www.nature.com/nm/journal/v18/n5/abs/nm.2736.html.
Jacoby E., et al., "Mitochondrial Augmentation of CD34+ Cells From Healthy Donors and Patients With Mitochondrial DNA Disorders Confers Functional Benefit," Npj Regenerative Medicine, 2021, vol. 6, No. 1, Article 58, 12 Pages, doi: 10.1038/s41536-021-00167-7, XP055876313, [Retrieved on Dec. 1, 2021] Retrieved from URL: https://www.nature.com/articles/s41536-021-00167-7.pdf.
Jacobye E., et al., "First-In Human Mitochondrial Augmentation of Hematopoietic Stem Cells in Pearson Syndrome," Blood, American Society of Hematology, US, Nov. 29, 2018, vol. 132, Supplement 1, p. 1024, 6 Pages, doi:10.1182/BLOOD-2018-99-113773, ISSN 0006-4971, XP086591032.
Jelenik T., et al., "Mitochondrial Plasticity in Obesity and Diabetes Mellitus," Antioxidants & Redox Signaling, 2013, vol. 19, No. 3, pp. 258-268.
Jenuth J.P., et al., "Random Genetic Drift in the Female Germline Explains the Rapid Segregation of Mammalian Mitochondrial DNA," Nature Genetics, 1996, vol. 14, No. 2, pp. 146-151.
Jenuth J.P., et al., "Tissue-Specific Selection for Different mtDNA Genotypes in Heteroplasmic Mice," Nature Genetics, 1997, vol. 16, No. 1, pp. 93-95.
Jeon S.Y., et al., "Comparison of Hair Shaft Damage After UVA and UVB Irradiation," The Journal of Cosmetic Science, Mar.-Apr. 2008, vol. 59, No. 2, pp. 151-156 (Abstract), 1 Page.
Katrangi E., et al., "Xenogenic Transfer of Isolated Murine Mitochondria Into Human p0 Cells Can Improve Respiratory Function," Rejuvenation Research, Dec. 2007, vol. 10, No. 4, pp. 561-570.
Keefe P., et al., "Fanconi Syndrome," StatPearls [Internet], Treasure Island (FL): StatPearls Publishing, NCBI Bookshelf, A service of the National Library of Medicine, National Institutes of Health, Jan. 2021, pp. 1-4.
Khasawneh et al., "A Novel Mitochondrial DNA Deletion in Patient with Pearson Syndrome" Med Arch., Apr. 2018, vol. 72, No. 2, pp. 148-150.
King M.P., et al., "Injection of Mitochondria Into Human Cells Leads To a Rapid Replacement of The Endogenous Mitochondrial DNA," Cell, vol. 52, No. 6, Mar. 25, 1988, pp. 811-819.
Kitani T., et al., "Direct Human Mitochondrial Transfer: A Novel Concept Based on the Endosymbiotic Theory," Transplantation Proceedings, 2014, vol. 46, No. 4, pp. 1233-1236.
Kitani T., et al., "Internalization of Isolated Functional Mitochondria: Involvement of Macropinocytosis," Journal of Cellular and Molecular Medicine, Apr. 2014, vol. 18, No. 8, pp. 1694-1703.
Klotzsch S.G., et al., "Triglyceride Measurements: A Review of Methods and Interferences," Clinical Chemistry, 1990, vol. 36, No. 9, pp. 1605-1613.
Kuranda K., et al., "Exposure to Wild-Type AAV Drives Distinct Capsid Immunity Profiles in Humans," Journal of Clinical Investigation, Dec. 3, 2018, vol. 128, No. 12, pp. 5267-5279, XP055927987.
Kuznetsov A.V., et al., "Cryopreservation of Mitochondria And Mitochondrial Function In Cardiac And Skeletal Muscle Fibers," Analytical Biochemistry, Sep. 2003, vol. 319. No. 2, pp. 296-303.
Lachgar S., et al., "Vascular Endothelial Growth Factor is an Autocrine Growth Factor for Hair Dermal Papilla Cells," The Journal of Investigative Dermatology, 1996, vol. 106, No. 1, pp. 17-23.
Larsen S., et al., "Biomarkers of Mitochondrial Content in Skeletal Muscle of Healthy Young Human Subjects," The Journal of physiology, 2012, vol. 590, No. 14, pp. 3349-3360.

(56)            References Cited

OTHER PUBLICATIONS

Lin C.S., et al., "Mouse mtDNA Mutant Model of Leber hereditary Optic Neuropathy," Proceedings of the National Academy of Sciences, 2012, vol. 109, No. 49, pp. 20065-20070.

Lin H.D., et al., "Human Wharton's Jelly Stem Cell Conditioned Medium Enhances Freeze-Thaw Survival and Expansion of Cryopreserved CD 34+ cells," Stem Cell Reviews and Reports, Apr. 2013, vol. 9, No. 2, pp. 172-183, XP055927986.

Lu Z., et al., "Profiling the Response of Human Hair Follicles to Ultraviolet Radiation," The Journal of Investigative Dermatology, 2009, vol. 129, No. 7, pp. 1790-1804.

"Maintenance of Mitochondrial Function by Nuclear NAD+ Levels and its Disruption by Aging," Vitamin, 2016, vol. 90, No. 10, pp. 502-507.

Makhlough A., et al., "Bone Marrow-Mesenchymal Stromal Cell Infusion In Patients With Chronic Kidney Disease: A Safety Study With 18 Months Of Follow-up," Cytotherapy, Feb. 2018, vol. 20, pp. 660-669.

Makris et al., "Mitochondriopathy of Peripheral Arterial Disease" 2007, Vascular 15(6):336-343.

Marcheque J., et al., "Concise Reviews: Stem Cells and Kidney Regeneration: An Update," Stem Cells Translational Medicine, 2019, vol. 8, pp. 82-92.

Martinez F., et al., "Structural And Functional Changes In Mitochondria Associated With Trophoblast Differentiation: Methods To Isolate Enriched Preparations of Syncytiotrophoblast Mitochondria," Endocrinology, May 31, 1999, vol. 138, No. 5, pp. 2172-2183, XP055144697.

Masuzawa et al., "Transplantation of Autologously Derived Mitochondria Protects the Heart from Ischemia-reperfusion Injury" Jan. 25, 2013, American Journal of Physiology—Heart and Circulatory Physiology 304(7):H966-H982.

McCully J.D., et al., "Injection of Isolated Mitochondria During Early Reperfusion For Cardioprotection," The American Journal of Physiology—Heart and Circulatory Physiology, Oct. 31, 2008, vol. 296, No. 1, 13 Pages, XP055144701.

Messenger A.G., et al., "Minoxidil: Mechanisms of Action on Hair Growth," British Journal of Dermatology, 2004, vol. 150, No. 2, pp. 186-194.

Mialet-Perez et al. "Cardiac monoamine oxidases: at the heart of mitochondrial dysfunction," Cell Death Dis, Jan. 23, 2020, vol. 11 (54), pp. 1-3, [retrieved on Apr. 11, 2022], retrieved from the Internet: URL: https://www.nature.com/articles/s41419-020-2251-4.pdf.

Modica-Napolitano J.S., et al., "Mitochondria As Targets For Detection And Treatment of Cancer," Expert Reviews in Molecular Medicine, Apr. 2002, vol. 4, No. 9, pp. 1-19.

Morley S.A., et al., "Plant Mitochondrial DNA," Frontiers in Bioscience, Landmark, Jan. 1, 2017, vol. 22, pp. 1023-1032.

Mracek et al,. "The Function and the Role of the Mitochondrial Glycerol-3-Phosphate Dehydrogenase in Mammalian Tissues," Biochimica et Biophysica Acta (BBA)—Bioenergetics, Dec. 7, 2012, vol. 1827(3), pp. 401-410, [retrieved on Apr. 11, 2022], retrieved from the Internet: URL: https://doi.org/10.1016/j.bbabio.2012.11.014.

Muftuoglu et al. "Mitochondrial Complex I and IV Dysfunction of Leukocytes in Parkinson's Disease" 2003, Turkish Journal of Biochemistry 28(4):246-251.

Muir R., et al., "Mitochondrial Content is Central to Nuclear Gene Expression: Profound Implications for Human Health," BioEssays, 2015, vol. 38, No. 2, pp. 150-156.

Murphy et al. "Allogeneic Endometrial Regenerative Cells: an Off the Shelf Solution" for Critical Limb Ischemia? Aug. 19, 2008, Journal of Translational Medicine 6(45):1-8.

Murthy M.S.R., et al., "Some Differences In The Properties Of Carnitine Palmitoyltransferase Activities Of The Mitochondrial Outer And Inner Membranes," Biochemical Journal, 1987, vol. 248, No. 3, pp. 727-733.

Nakamura K., et al., "Characterization Of Bioactive Agents In Five Types Of Marketed Sprouts And Comparison Of Their Antihyper-tensive, Antihyperlipidemic, And Antidiabetic Effects In Fructose-Loaded SHRs," Journal of Food Science and Technology, 2016, vol. 53, No. 1, pp. 581-590.

Neste D.V., et al., "Finasteride Increases Anagen Hair in Men with Androgenetic Alopecia," British Journal of Dermatology, 2000, vol. 143, No. 4, pp. 804-810.

Noterman M.F., et al., "Dual-Process Brain Mitochondria Isolation Preserves Function And Clarifies Protein Composition," PNAS, Feb. 2, 2021, vol. 118, No. 11, pp. 1-10.

Office Action for European Application No. 16754857.7, mailed May 4, 2022, 10 Pages.

Office Action for European Patent Application No. 12830575.2, mailed Mar. 16, 2017, 4 Pages.

Office Action for European Patent Application No. 12830575.2, mailed Feb. 24, 2016, 10 Pages.

Office Action for European Patent Application No. 12830575.2, mailed Oct. 25, 2016, 8 Pages.

Office Action for European Patent Application No. 12830575.2, mailed Sep. 28, 2015, 7 Pages.

Office Action for European Patent Application No. 16754857.7, mailed Jun. 6, 2019, 4 Pages.

Office Action for European Patent Application No. 19841655.4, mailed Jun. 28, 2023, 17 Pages.

Office action for Israel Patent Application No. 299482, mailed Jun. 22, 2023, 6 pages.

Office Action for Japanese Patent Application No. 2020551356, mailed Feb. 7, 2023, 11 Pages.

Office Action for Japanese Patent Application No. 2021502763, mailed Mar. 20, 2023, 14 Pages.

Office Action for Japanese Patent Application No. 2021502765, mailed Jun. 27, 2023, 11 Pages.

Office Action for Japanese Patent Application No. 2021502783, mailed Jun. 27, 2023, 10 Pages.

Office Action for Japanese Patent Application No. 2021-502836, mailed Mar. 20, 2023, 13 Pages.

Office Action for Japanese Patent Application No. 2021502844, mailed Jul. 4, 2023, 16 Pages.

Office Action for Japanese Patent Application No. 2021502870, mailed Jun. 27, 2023, 10 Pages.

Office Action for Japanese Patent Application No. 2021502879, mailed Jun. 27, 2023, 19 Pages.

Office Action for Japanese Patent Application No. 2021503582, mailed Jun. 27, 2023, 16 Pages.

Parone P.A., et al., "Preventing Mitochondrial Fission Impairs Mitochondrial Function And Leads To Loss Of Mitochondrial DNA," PLOS One, Feb. 2008, vol. 3, No. 9, 9 Pages.

Pasquier J., et al., "Preferential Transfer of Mitochondria From Endothelial to Cancer Cells Through Tunneling Nanotubes Modulates Chemoresistance," Journal of Translational Medicine, Apr. 10, 2013, vol. 11, No. 94, 14 Pages, XP021151199, Retrieved from URL: http://download.springer.com/static/pdf/438/art%253A10.1186%252F1479-5876-11-94.pdf?originUrl=http%3A%2F%2Ftranslational-medicine.biomedcentral.com%2Farticle%2F10.1186%2F1479-5876-11-94&token2=exp=1465970179~acl=%2Fstatic%2Fpdf%2F438%2Fart%25253A10.1186%25252F1479-5876-11-94.pdf*~hmac=9ddc595d5.

Piel et al. "Exogenous Cytochrome C Restores Myocardial Cytochrome Oxidase Activity into the Late Phase of Sepsis" 2008, Shock 29(5):612-616.

Piel et al. "Mitochondrial Resuscitation with Exogenous Cytochrome C in the Septic Heart" 2007, Critical Care Medicine 35(9):2120-2127.

Pinkert C.A., et al., "Mitochondria Transfer Into Mouse Ova By Microinjection," Transgenic Research, Nov. 1997, vol. 6, No. 6, pp. 379-383.

Pipino C., et al., "Placenta As A Reservoir of Stem Cells: An Underutilized Resource?," British Medical Bulletin, Nov. 25, 2012, vol. 105, No. 1, pp. 1-25.

Platzbecker et al., "Treatment of MDS," Blood, The Journal of the American Society of Hematology, 2019, vol. 133, No. 10, pp. 1096-1107.

(56) References Cited

OTHER PUBLICATIONS

Plotnikov E.Y., et al., "Cytoplasm And Organelle Transfer Between Mesenchymal Multipotent Stromal Cells And Renal Tubular Cells In Co-culture," Experimental Cell Research, Sep. 10, 2010, vol. 316, No. 15, pp. 2447-2455.

Renaghan A.D., et al., "Acute Kidney Injury and CKD Associated with Hematopoietic Stem Cell Transplantation," CJASN, Feb. 2020, vol. 15, pp. 289-297.

Romero-Moya D., et al., "Cord Blood-Derived CD34+ Hematopoietic Cells With Low Mitochondrial Mass Are Enriched in Hematopoietic Repopulating Stem Cell Function," Haematologica, 2013, vol. 98, No. 7, pp. 1022-1029.

Rota C., et al., "Stem Cell Therapies in Kidney Diseases: Progress and Challenges," International Journal of Molecular Sciences, Jun. 7, 2019, vol. 20, Article 2790, pp. 1-26.

Roushandeh A.M., et al., "Mitochondrial Transplantation as a Potential and Novel Master Key for Treatment of Various Incurable Diseases," Cytotechnology, 2019, vol. 71, No. 2, pp. 647-663.

Rousou A.J., et al., "Opening of Mitochondrial KATP Channels Enhances Cardioprotection Through The Modulation of Mitochondrial Matrix Volume, Calcium Accumulation, And Respiration," American Journal of Physiology-Heart and Circulatory Physiology, Jul. 8, 2004, vol. 287, No. 5, pp. H1967-H1976, XP055144706.

Saely C.H., et al., "Brown versus White Adipose Tissue: A Mini-Review," Gerontology, 2012, 58(1), pp. 15-23.

Satoh et al. "Mitochondrial Damage-induced Impairment of Angiogenesis in the Aging Rat Kidney" Feb. 2011, Laboratory Investigation 91(2):190-202.

Schechner et al. "Engraftment of a Vascularized Human Skin Equivalent" Dec. 2003, FASEB Journal 17(15):2250-2256.

Sebetic K., et al., "UV Damage of the Hair," Collegium Antropologicum, 2008, vol. 32 Supplement.2, pp. 163-165.

Shah S.N., et al., "Serum Bicarbonate Levels and the Progression of Kidney Disease: A Cohort Study," American Journal of Kidney Diseases, Aug. 2009, vol. 54, No. 2, pp. 270-277.

Shi J., et al., "Mitochondria Transfer Into Fibroblasts: Liposome-Mediated Transfer of Labeled Mitochondria Into Cultured Cells," Ethnicity and Disease, Mar. 2008, vol. 18, No. 2, pp. S1-43-S1-44.

Shimoji H., et al., "Inhibitory Effects of Flavonoids on Alternative Respiration of Plant Mitochondria," Biologia Plantarum, 2005, vol. 49, No. 1, pp. 117-119.

Shin et al., "Mitochondrial DNA Mutations in Patients with Myelodysplastic Syndromes", Blood, The Journal of the American Society of Hematology, 2003, vol. 101, No. 8, pp. 3118-3125.

Sidney L.E., et al., "Concise Review: Evidence for CD34 as a Common Marker for Diverse Progenitors," Stem Cells, 2014, vol. 32, No. 6, pp. 1380-1389.

Sivitz W.I., et al., "Mitochondrial Dysfunction In Obesity And Diabetes," US Endocrinology, Dec. 31, 2010, vol. 6, No. 1, pp. 20-27, DOI: 1 0.17925/USE.201 0.06.1.20, XP055729849.

Smith et al. "Locally Enhanced Angiogenesis Promotes Transplanted Cell Survival" 2004,Tissue Engineering 10(1-2):63-71 (11 pages).

Smith L.J., et al., "Stem Cell-Derived Clade F AAVs Mediate High-Efficiency Homologous Recombination-Based Genome Editing," Proceedings of the National Academy of Sciences of the United States of America, Jul. 31, 2018, vol. 115, No. 31, DOI: 10.1073/pnas.1802343115, pp. E7379-E7388, XP055609078.

Snyder C., et al., "Mitochondria and Chloroplasts Shared in Animal and Plant Tissues: Significance of Communication," Medical Science Monitor, 2015, vol. 21, pp. 1507-1511.

Spees J.L., et al., "Mitochondrial Transfer Between Cells Can Rescue Aerobic Respiration," Proceedings Of The National Academy Of Sciences, US, Jan. 31, 2006, vol. 103, No. 5, pp. 1283-1288, doi:10.1073/pnas.0510511103, ISSN 0027-8424, XP055349990.

Stork C., et al., "Mitochondrial Dysfunction in Bipolar Disorder: Evidence From Magnetic Resonance Spectroscopy Research," Molecular Psychiatry, 2005, vol. 10, No. 10, pp. 900-919.

Swaminathan M., et al., "Allogeneic Mesenchymal Stem Cells for Treatment of AKI after Cardiac Surgery," Journal of the American Society of Nephrology, 2018, vol. 29, 20 Pages.

Szewczyk A., et al., "Mitochondria as a Pharmacological Target," Pharmacological Reviews, Mar. 2002, vol. 54, No. 1, pp. 101-127.

Tachibana M., et al., "Mitochondrial Gene Replacement in Primate Offspring and Embryonic Stem Cells," Nature, Sep. 17, 2009, vol. 461, No. 7262:367-372, 15 Pages, doi: 10.1038/nature08368, XP055072881, Retrieved from URL: http://www.nature.com/nature/journal/v461/n7262/abs/nature08368.html.

Takeda K., et al., "Microinjection of Cytoplasm or Mitochondria Derived From Somatic Cells Affects Parthenogenetic Development of Murine Oocytes," Biology of Reproduction, Feb. 16, 2005, vol. 72, No. 6, pp. 1397-1404.

Tang K.W.A., et al., "Normalisation of Urinary Biomarkers to Creatinine for Clinical Practice and Research—When and Why," Singapore Medical Journal, 2015, vol. 56, No. 1, pp. 7-10.

The Champ Foundation, "William's blog., Let's get MORE Research Started," Fighting against Pearson Syndrome, May 1, 2017, 4 pages.

Tian L., et al., "Impaired Mitochondrial Function Results from Oxidative Stress in the Full-Term Placenta of Sows with Excessive Back-Fat," Animals, Feb. 2020, vol. 10, No. 360, pp. 1-19.

Torralba D., et al., "Mitochondria Know No Boundaries: Mechanisms and Functions of Intercellular Mitochondrial Transfer," Front Cell Dev Biol., Sep. 2016, vol. 4, 11 pages.

Tuckey R.C., et al., "The Concentration Of Adrenodoxin Reductase Limits Cytochrome P450scc Activity In The Human Placenta," European Journal of Biochemistry, Jul. 31, 1999, vol. 263, No. 2, pp. 319-325, XP055144683.

Tuckey R.C., "Progesterone Synthesis by the Human Placenta," Placenta, May 2005, vol. 26, No. 4, pp. 273-281.

Van Blerkom J., et al., "Mitochondrial Transfer Between Oocytes: Potential Applications Of Mitochondrial Donation And The Issue Of Heteroplasmy," Human Reproduction, Nov. 1998, vol. 13, No. 10, pp. 2857-2868.

Vormann J., "Magnesium and Kidney Health—More on the 'Forgotten Electrolyte'," American Journal of Nephrology, 2016, vol. 44, pp. 379-380.

Wagle M.A., et al., "The Utility Of An Isolated Mitochondrial Fraction In The Preparation Of Liposomes For The Specific Delivery Of Bioactives To Mitochondria In Live Mammalian Cells," Pharmaceutical Research, Jul. 15, 2011, vol. 28, No. 11, pp. 2790-2796.

Wang W., et al., "Novel Targets for Mitochondrial Medicine," Science Translational Medicine, vol. 8, No. 326, Feb. 17, 2016, 17 pages, Retrieved from the Internet: https://www.ncbi.nlm.nih.gov/pmc/articles/PMC4819426/pdf/nihms769346.pdf.

Wei Y., et al., "Nonalcoholic Fatty Liver Disease and Mitochondrial Dysfunction," World J Gastroenterol, Jan. 14, 2008, vol. 14, No. 2, pp. 193-199.

Weiss J.N., et al., "Stem Cell Ophthalmology Treatment Study: Bone Marrow Derived Stem Cells in the Treatment of Retinitis Pigmentosa," Stem Cell investigation, Jun. 6, 2018, vol. 5, No. 18, pp. 1-9, doi: 10.21037/sci.2018.04.02, XP055778156.

Wieckowski M.R., et al., "Isolation Of Mitochondria-Associated Membranes And Mitochondria From Animal Tissues And Cells," Nature Protocol, Oct. 8, 2009, vol. 4, No. 11, pp. 1582-1590.

Xu Y., et al., "Efficient Commitment To Functional CD34+ Progenitor Cells From Human Bone Marrow Mesenchymal Stem-cell-derived Induced Pluripotent Stem Cells," PLoS One, vol. 7, No. 4, 2012, e34321,10 Pages.

Yamagata K., et al., "Pathological Roles of Mitochondrial Dysfunction in Podocyte Injury," The Japanese Journal of Nephrology, 2007, vol. 49, No. 2, pp. 82-87.

Yamaguchi R., et al., "Mitochondria Frozen With Trehalose Retain A Number Of Biological Functions And Preserve Outer Membrane Integrity," Cell Death Differentiation, Copyright Year: 2007, Published Online: Sep. 15, 2006, vol. 14, No. 3, pp. 616-624, XP055144699.

Yang C-H., et al., "Safety And Efficacy Of Intrarenal Arterial Autologous Cd34+ Cell Transfusion In Patients With Chronic Kidney Disease: A Randomized, Open-label, Controlled Phase II Clinical Trial," Stem Cells Translational Medicine, Mar. 2020, vol. 9, pp. 827-838.

(56)            References Cited

OTHER PUBLICATIONS

Yasuda K., et al., "Tunneling Nanotubes Mediate Rescue Of Prematurely Senescent Endothelial Cells By Endothelial Progenitors: Exchange Of Lysosomal Pool," Aging, Jun. 2011, vol. 3, No. 6, pp. 597-608.

You Y., et al., "Mulberry and Mulberry Wine Extract Increase the Number of Mitochondria During Brown Adipogenesis," Food & Function, Feb. 2015, vol. 6, No. 2, pp. 401-408.

Yu J., et al., "Induced Pluripotent Stem Cell Lines Derived From Human Somatic Cells," Science, Dec. 21, 2007, vol. 318, No. 5858, pp. 1917-1920.

Zhang Y., et al., "Deletion of a 4977-bp Fragment in the Mitochondrial Genome is Associated With Mitochondrial Disease Severity," PloS One, May 29, 2015, vol. 10, No. 5: e0128624, 10 Pages, XP055549866, Retrieved from URL: http://journals.plos.org/plosone/article?id=10.1371/journal, pone.0128624.

Zheng Y., et al., "Mitochondrial DNA 4977 bp Deletion is a Common Phenomenon in Hair and Increases with Age," Bosn Journal of Basic Medical Sciences, 2012, vol. 12, No. 3, pp. 187-192.

* cited by examiner

Mitochondrially enriched CAR-T cells: Day 10

ATP content

Citrate Synthase Activity

% Viability

FIGURE 1B

MITOCHONDRIA-ENRICHED GENETICALLY ENGINEERED CELLS AND USES THEREOF

CROSS-REFERENCE TO RELATED APPLICATIONS

This application is a 35 USC § 371 National Stage application of International Application No. PCT/IL2021/050358 filed Mar. 30, 2021, which claims the benefit under 35 USC § 119(e) to U.S. Application Ser. No. 63/003,184 filed Mar. 31, 2020. The disclosure of each of the prior applications is considered part of and is incorporated by reference in the disclosure of this application.

BACKGROUND OF THE INVENTION

Field of the Invention

The present invention relates generally to pharmaceutical compositions and methods of treatment using genetically engineered cells, and more specifically to genetically engineered lymphocytes enriched with mitochondria.

Background Information

Despite tremendous advances in medicine and treatment approaches, cancer remains one of the most life-threatening diseases in industrialized countries. While the combination of standard therapeutic strategies, e.g., surgery, chemotherapy and radiation, can in most cases be efficient for treatment of primary tumors, these strategies often fail to successfully treat metastatic tumors and prevent the progression of the disease through disseminated tumor cells. Recently, cell-based immunotherapy, in particular adoptive transfer of T lymphocytes, has emerged as a highly potential alternative modality for cancer treatment, aiming to prevent the metastatic spread of the disease and to improve quality of life of subjects with late-stage disease, including those who are refractory to standard therapies. T-cell based immunotherapy takes advantage of the natural ability of T-cells to penetrate tissues, become activated and eliminate target cells. Genetically engineered T-cells (e.g., T-cell receptor (TCR) and chimeric antigen receptor (CAR)-transduced T cells) that specifically recognize antigen targets expressed on cancer cells, have been employed in clinical trials and have achieved promising results.

The spectrum of T cell-based therapy is further being expanded to include autoimmune disorders. Preliminary results of preclinical and clinical studies support the application of CAR T therapy in autoimmunity, especially in regulating adverse autoimmune responses.

The T-cell receptor (TCR) is a molecule found on the surface of T cells, or T lymphocytes, that is responsible for recognizing fragments of antigen as peptides bound to major histocompatibility complex (MHC) molecules. The binding between TCR and antigen peptides is of relatively low affinity and is degenerate: that is, many TCRs recognize the same antigen peptide and many antigen peptides are recognized by the same TCR.

The TCR is composed of two different protein chains. In humans, in 95% of T cells the TCR consists of an alpha ($\alpha$) chain and a beta ($\beta$) chain (encoded by TRA and TRB, respectively), whereas in 5% of T cells the TCR consists of gamma and delta ($\gamma/\delta$) chains (encoded by TRG and TRD, respectively). This ratio changes during ontogeny and in diseased states (such as leukemia). It also differs between species. Orthologues of the 4 loci have been mapped in various species.

The mitochondrion, a membrane bound organelle ranging from 0.5 to 1.0 µm in diameter, supplies cellular energy and plays a central role in the metabolic function of the cell. Mitochondria are found in nearly all eukaryotic cells and vary in number and location depending on the cell type. Mitochondria contain their own DNA (mtDNA) and their own machinery for synthesizing RNA and proteins. The mtDNA contains only 37 genes, thus most of the gene products in the mammalian body are encoded by nuclear DNA.

The primary function of mitochondria is the generation of energy as adenosine triphosphate (ATP) by means of the electron-transport chain and the oxidative-phosphorylation system (the "respiratory chain"). In addition, mitochondria perform numerous essential tasks in the eukaryotic cell such as pyruvate oxidation, the Krebs cycle and metabolism of amino acids, fatty acids and steroids. Additional processes in which mitochondria are involved include heat production, storage of calcium ions, calcium signaling, programmed cell death (apoptosis) and cellular proliferation.

The ATP concentration inside the cell is typically 1-10 mM. ATP can be produced by redox reactions using simple and complex sugars (carbohydrates) or lipids as an energy source. For complex fuels to be synthesized into ATP, they first need to be broken down into smaller, simpler molecules. Complex carbohydrates are hydrolyzed into simple sugars, such as glucose and fructose. Fats (triglycerides) are metabolized to give fatty acids and glycerol.

The overall process of oxidizing glucose to carbon dioxide is known as cellular respiration and can produce about 30 molecules of ATP from a single molecule of glucose. ATP can be produced by a number of distinct cellular processes. The three main pathways used to generate energy in eukaryotic organisms are glycolysis and the citric acid cycle/oxidative phosphorylation, both components of cellular respiration, and beta-oxidation. The majority of this ATP production by non-photosynthetic eukaryotes takes place in the mitochondria, which can make up nearly 25% of the total volume of a typical cell.

Attempts to induce transfer of mitochondria into host cells or tissues have been reported. Most methods require active transfer of the mitochondria by injection. Transfer of mitochondria engulfed within a vehicle, such as a liposome, is also known. It has been further shown that mitochondrial transfer may occur spontaneously between cells in vitro although it was only established that mtDNA was transferred rather than intact whole mitochondria. Mitochondrial transfer in vitro by endocytosis or internalization has been demonstrated as well.

SUMMARY OF THE INVENTION

The present invention is based on the seminal discovery that cells enriched with mitochondria are useful for treating diseases and disorders. The present invention provides pharmaceutical compositions of mitochondrially-enriched, genetically engineered T cells. The present invention also provides methods of treatment using mitochondrially-enriched genetically engineered T cells.

In one embodiment the present invention provides a pharmaceutical composition including mitochondrially-enriched, genetically engineered T cells and a pharmaceutically acceptable carrier, wherein the mitochondrially-enriched genetically engineered T cells are enriched with exogenous mitochondria.

In one aspect, the mitochondrially-enriched genetically engineered T cells are produced by the method including obtaining T cells from a subject afflicted with a disease or disorder or a donor; obtaining exogenous mitochondria; producing mitochondrially-enriched T cells by contacting the T cells with the exogenous mitochondria under conditions allowing the exogenous mitochondria to enter the T cells; and producing mitochondrially-enriched genetically engineered T cells by introducing a nucleic acid encoding a chimeric T cell receptor (TCR) or chimeric antigen receptor (CAR) into the mitochondrially-enriched T cells, wherein the mitochondrial content of the mitochondrially-enriched genetically engineered T cells is detectably higher than the mitochondrial content of the T cells. In one embodiment, the conditions allowing exogenous mitochondria to enter the T cells includes incubating the T cells with the exogenous mitochondria at a ratio of about 0.088-176 mU citrate synthase (CS) activity per $10^6$ T cells.

In an additional aspect, the mitochondrially-enriched genetically engineered T cells are produced by the method including obtaining T cells from a subject afflicted with a disease or disorder or a donor; producing genetically engineered T cells by introducing a nucleic acid encoding a chimeric T cell receptor (TCR) or chimeric antigen receptor (CAR) into the T cells, obtaining exogenous mitochondria; and producing mitochondrially-enriched genetically engineered T cells by contacting the genetically engineered T cells with the exogenous mitochondria under conditions allowing the exogenous mitochondria to enter the genetically engineered T cells; wherein the mitochondrial content of the mitochondrially-enriched genetically engineered T cells is detectably higher than the mitochondrial content of the genetically engineered T cells. In one aspect, the conditions allowing exogenous mitochondria to enter the genetically engineered T cells includes incubating the genetically engineered T cells with the exogenous mitochondria at a ratio of about 0.088-176 mU citrate synthase (CS) activity per $10^6$ T cells.

In certain aspects, the genetically engineered T cells and mitochondrially-enriched genetically engineered T cells are CAR-T cells. In another aspect, the genetically engineered T cells and mitochondrially-enriched T-cells are TCR-T cells. In various aspects, the exogenous mitochondria are derived from a human cell. In some embodiments, the human cell is from a human placenta, human blood cells, human stem cells or human somatic cells. In some embodiments, the human cell are cells grown in culture. In certain aspect, the stem cells are induced pluripotent stem cells, embryonic stem cells or pluripotent cells. In another aspect, the exogenous human mitochondria are syngeneic or allogeneic. In a further aspect, the exogenous mitochondria are autologous.

In one aspect, the pharmaceutical composition has at least $1×10^5$ to $5×10^{10}$ mitochondrially-enriched T cells or mitochondrially-enriched genetically engineered T-cells cells per Kg body weight of a subject in need thereof. In some embodiments, dose escalation is performed.

In certain aspects, the mitochondrially-enriched genetically-engineered T-cells have at least one of an increased mitochondrial DNA content; an increased level of citrate synthase (CS) activity; an increased content of at least one mitochondrial protein selected from SDHA and COX1; an increased rate of $O_2$ consumption; an increased rate of ATP production; or any combination thereof relative to the corresponding level in the T-cells prior to mitochondrial enrichment.

In various aspects, the conditions allowing the exogenous mitochondria to enter the T cells or genetically engineered T cells comprise incubating the T cells or genetically engineered T cells with the exogenous mitochondria for a time ranging from about 0.5 to 30 hours at a temperature ranging from about 16 to 37° C. In an additional aspect, the exogenous mitochondria constitute above 1% of the total mitochondria content in the mitochondrially-enriched T cells or mitochondrially-enriched genetically engineered T-cells.

In one aspect, the disease or disorder is cancer. In specific aspects, the cancer is hematological cancer. In another aspect, the T cells are autologous or allogenic.

In an additional embodiment, the present invention provides a method of treating a disease or disorder in a subject in need thereof including administering mitochondrially-enriched genetically engineered T cells to the subject, wherein the mitochondrially-enriched genetically engineered T cells are enriched with exogenous mitochondria.

In one aspect, the mitochondrially-enriched genetically engineered T cells are produced by the method including obtaining T cells from a subject afflicted with a disease or disorder or a donor; obtaining exogenous mitochondria; producing mitochondrially-enriched T cells by contacting the T cells with the exogenous mitochondria under conditions allowing the exogenous mitochondria to enter the T cells; and producing mitochondrially-enriched genetically engineered T cells by introducing a nucleic acid encoding a chimeric T cell receptor (TCR) or chimeric antigen receptor (CAR) into the mitochondrially-enriched T cells, wherein the mitochondrial content of the mitochondrially-enriched genetically engineered T cells is detectably higher than the mitochondrial content of the T cells. In some embodiments, the mitochondrial content of the mitochondrially-enriched genetically engineered T cells is detectably higher than the mitochondrial content of the T cells. In one aspect, the conditions allowing exogenous mitochondria to enter the T cells includes incubating the T cells with the exogenous mitochondria at a ratio of about 0.088-176 mU citrate synthase (CS) activity per $10^6$ T cells.

In an additional aspect, the mitochondrially-enriched genetically engineered T cells are produced by the method including obtaining T cells from a subject afflicted with a disease or disorder or a donor; producing genetically engineered T cells by introducing a nucleic acid encoding a chimeric T cell receptor (TCR) or chimeric antigen receptor (CAR) into the T cells, obtaining exogenous mitochondria from a donor; and producing mitochondrially-enriched genetically engineered T cells by contacting the genetically engineered T cells with the exogenous mitochondria under conditions allowing the exogenous mitochondria to enter the genetically engineered T cells; wherein the mitochondrial content of the mitochondrially-enriched genetically engineered T cells is detectably higher than the mitochondrial content of the genetically engineered T cells. In one aspect, the conditions allowing exogenous mitochondria to enter the genetically engineered T cells includes incubating the genetically engineered T cells with the exogenous mitochondria at a ratio of about 0.088-176 mU citrate synthase (CS) activity per $10^6$ T cells.

In one aspect, the subject is a human subject. In another aspect, the disease or disorder is cancer. In a specific aspect, the cancer is a hematological cancer. In certain aspects, the administration is by intravenous, intraperitoneal, intraarterial, intrathecal, and intramuscular administration. In one aspect, the administration is by intravenous administration.

In an additional aspect, the method of treating also includes administering a chemotherapeutic agent, radiation or other anti-cancer therapy to the subject. In a further aspect, the pharmaceutical composition is administered simultaneously, concurrently or following administration of the chemotherapeutic agent, radiation or other anti-cancer therapy. In certain aspects, the exogenous mitochondria are derived from a human cell. In some embodiments, the human cell is from a human placenta, human blood cells, stem cells or a somatic cell. In some embodiments, the human cell are cells grown in culture. In certain aspect, the stem cells are induced pluripotent stem cells, embryonic stem cells or pluripotent cells. In certain aspects, the exogenous mitochondria are allogenic or autologous. In one aspect, following enrichment by the exogenous mitochondria at least 1% of the total mitochondria content in the mitochondrially-enriched T cells or mitochondrially-enriched genetically engineered T-cells comprises exogenous mitochondria. In various aspects, the conditions allowing the exogenous mitochondria to enter the T cells, or genetically engineered T cells comprise incubating the T cells, or genetically engineered T cells with the exogenous mitochondria for a time ranging from 0.5 to 30 hours at a temperature ranging from about 16 to 37° C.

BRIEF DESCRIPTION OF THE DRAWINGS

FIGS. 1A-C show mitochondrially enriched CAR-T cells. FIG. 1A: shows ATP levels and Citrate synthase activity of CAR-T cells enriched with mitochondria 5 days after cell activation. FIG. 1B shows ATP levels and Citrate synthase activity of CAR-T cells enriched with mitochondria 10 days after cell activation. FIG. 1C shows percent of exogenous mtDNA measured in CAR-T cells enriched with 4.4 mU mitochondria on day 5 and day 10 of cell activation.

DETAILED DESCRIPTION OF THE INVENTION

Figure 1A:
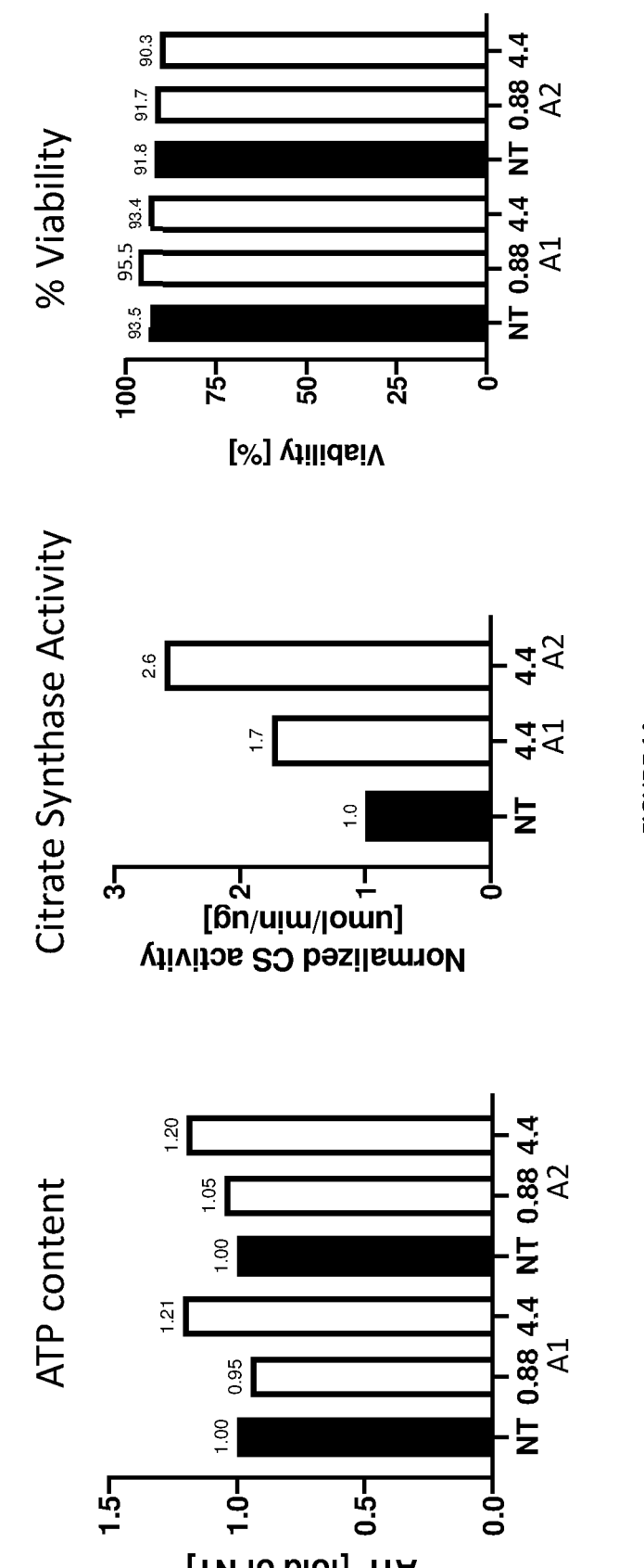

The present invention is based on the seminal discovery that cells enriched with mitochondria are useful for treating diseases and disorders. The present invention provides pharmaceutical compositions of mitochondrially-enriched genetically engineered T cells. The present invention also provides methods of treatment using mitochondrially-enriched genetically engineered T cells.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, it will be understood that modifications and variations are encompassed within the spirit and scope of the instant disclosure. The preferred methods and materials are now described.

The present invention provides pharmaceutical compositions and uses thereof for immunotherapy of cancer, the pharmaceutical compositions comprising human mature lymphocytes, including non-genetically modified lymphocytes and genetically modified lymphocytes (e.g., CAR T-cells) which have been enriched ex vivo with exogenous mitochondria.

The term "lymphocytes" as used herein refers to white blood cells that play a major role in defending the body against disease, and includes T-cells, natural killer cells (NK cells), B-cells and mixtures thereof. It will be appreciated by one of skill in the art that the above listed immune cell types can be divided into further subsets. In some embodiments, the lymphocytes are mature lymphocytes. In some embodiments, the lymphocytes are non-genetically modified lymphocytes. In other embodiments, the lymphocytes are genetically modified lymphocytes.

The term "mature lymphocytes" as used herein refers to fully differentiated or terminally differentiated lymphocytes that experienced the development that lead to the selection and maturation in the central lymphoid tissue. Following maturation, the lymphocytes enter the circulation and peripheral lymphoid organs (e.g. the spleen and lymph nodes). According to some embodiments, the term "mature lymphocytes" does not include lymphoid progenitor cells or lymphocyte precursor cells. According to other embodiments, the term "mature lymphocytes" encompass also lymphocytes precursor cells. The term "lymphocytes precursor cells" as used herein refers to partially differentiated unipotent cells which usually constitute the intermediate cells before they become differentiated to lymphocytes. The term "unipotent" as used herein refers to cells that have the capacity to differentiate into only one cell type. As opposed to precursor cells, progenitor cells are multipotent, having the potential to differentiate into discrete cell types.

Maturity of cells can be evaluated based on assays such as marker expression, function, integration and non-division. For example, with respect to T cells, a mature T cell is characterized by the expression of either CD4 or CD8, but not both (i.e., they are single positive), and expression of CD3. Expression of such markers can be determined by methods known in the art, for example, by FACS analysis or immunohistological staining techniques.

The T-cell receptor (TCR) is a protein complex found on the surface of T cells, or T lymphocytes, that is responsible for recognizing fragments of antigen as peptides bound to major histocompatibility complex (MHC) molecules. The binding between TCR and antigen peptides is of relatively low affinity and is degenerate. The TCR is composed of two different protein chains. In humans, in 95% of T cells the TCR consists of an alpha (α) chain and a beta (β) chain (encoded by TRA and TRB, respectively), whereas in 5% of T cells the TCR consists of gamma and delta (γ/δ) chains (encoded by TRG and TRD, respectively). This ratio changes during ontogeny and in diseased states (such as leukemia). The antigenic molecules that activate γδ T cells are still mostly unknown. However, γδ T cells are not MHC-restricted and seem to be able to recognize whole proteins rather than requiring peptides to be presented by MHC molecules on APCs. Human γδ T cells which use the Vγ9 and Vδ2 gene fragments constitute the major γδ T cell population in peripheral blood.

The present invention is based in part on the finding that T-lymphocytes are receptive to being enriched with exogenous mitochondria, and that enriching lymphocytes with exogenous mitochondria can increase mitochondrial content, cell survival, fatty acid oxidation (FAO) and ATP production. Without being bound to any theory or mechanism, it is postulated that co-incubation of lymphocytes with exogenous mitochondria promotes the transition of intact mitochondria into the lymphocytes. It is further hypothesized that ameliorating lymphocytes' mitochondrial functionality by mitochondrial enrichment can improve the in vivo functionality of the lymphocytes post transplantation, thereby enhancing cell-based immunotherapy.

The term "cell-based immunotherapy" as used herein relates to a therapy comprising application of genetically-modified or non-genetically modified immune cells, e.g. T-cells, to a subject. This therapeutic approach can be used to treat a wide range of cancer diseases, as well as infectious diseases and autoimmune disorders.

The present invention provides a pharmaceutical composition including mitochondrially-enriched genetically engineered T cells and a pharmaceutically acceptable carrier, wherein the genetically engineered T cells are enriched with exogenous mitochondria. The present invention also provides a method of treatment of a subject in need thereof including administering mitochondrially-enriched genetically engineered T cells to the subject, wherein the mitochondrially-enriched genetically engineered T cells are enriched with exogenous mitochondria.

As used herein, "pharmaceutical composition" refers to a formulation comprising an active ingredient, and optionally a pharmaceutically acceptable carrier, diluent or excipient. The term "active ingredient" can interchangeably refer to an "effective ingredient", and is meant to refer to any agent that is capable of inducing a sought-after effect upon administration. Examples of active ingredient include, but are not limited to, chemical compound, drug, therapeutic agent, small molecule, etc.

By "pharmaceutically acceptable" it is meant the carrier, diluent or excipient must be compatible with the other ingredients of the formulation and not deleterious to the recipient thereof, nor to the activity of the active ingredient of the formulation. Pharmaceutically acceptable carriers, excipients or stabilizers are well known in the art, for example Remington's Pharmaceutical Sciences, 16th edition, Osol, A. Ed. (1980). Pharmaceutically acceptable carriers, excipients, or stabilizers are nontoxic to recipients at the dosages and concentrations employed, and may include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (for example, Zn-protein complexes); and/or non-ionic surfactants such as TWEEN™, PLURONICS™ or polyethylene glycol (PEG). Examples of carrier include, but are not limited to, liposome, nanoparticles, ointment, micelles, microsphere, microparticle, cream, emulsion, and gel. Examples of excipient include, but are not limited to, anti-adherents such as magnesium stearate, binders such as saccharides and their derivatives (sucrose, lactose, starches, cellulose, sugar alcohols and the like) protein like gelatin and synthetic polymers, lubricants such as talc and silica, and preservatives such as antioxidants, vitamin A, vitamin E, vitamin C, retinyl palmitate, selenium, cysteine, methionine, citric acid, sodium sulfate and parabens. Examples of diluent include, but are not limited to, water, alcohol, saline solution, glycol, mineral oil and dimethyl sulfoxide (DMSO).

The term "treatment" is used interchangeably herein with the term "therapeutic method" and refers to both 1) therapeutic treatments or measures that cure, slow down, lessen symptoms of, and/or halt progression of a diagnosed pathologic conditions or disorder, and 2) and prophylactic/preventative measures. Those in need of treatment may include individuals already having a particular medical disorder as well as those who may ultimately acquire the disorder (i.e., those needing preventive measures).

The terms "therapeutically effective amount", "effective dose," "therapeutically effective dose", "effective amount," or the like refer to that amount of the subject compound that will elicit the biological or medical response of a tissue, system, animal or human that is being sought by the researcher, veterinarian, medical doctor or other clinician. The effective amount can be determined as described herein.

The terms "administration of" and or "administering" should be understood to mean providing a pharmaceutical composition in a therapeutically effective amount to the subject in need of treatment. Administration routes can be enteral, topical or parenteral. As such, administration routes include but are not limited to intravenous, intraperitoneal, intraarterial, intrathecal, and intramuscular administration. The phrases "parenteral administration" and "administered parenterally" as used herein means modes of administration other than enteral and topical administration. The pharmaceutical compositions can be administered in a variety of unit dosage forms depending upon the method of administration. Suitable unit dosage forms, include, but are not limited to capsules, injectables, implantable sustained-release formulations, and lipid complexes.

In certain aspects, the mitochondrially-enriched genetically engineered T cells are produced by the method of obtaining T cells from a subject afflicted with a disease or disorder or a donor; obtaining exogenous mitochondria; producing mitochondrially-enriched T cells by contacting the T cells with the exogenous mitochondria under conditions allowing the exogenous mitochondria to enter the T cells; and producing mitochondrially-enriched genetically engineered T cells by introducing a nucleic acid encoding a chimeric T cell receptor (TCR) or chimeric antigen receptor (CAR) into the mitochondrially-enriched genetically engineered T cells, wherein the mitochondrial content of the mitochondrially-enriched genetically engineered T cells is detectably higher than the mitochondrial content of the T cells. In certain aspects, the conditions allowing the exogenous mitochondria to enter the T cells includes contacting the T cells with the exogenous mitochondria at a ratio of about 0.088-176 mU citrate synthase (CS) activity per $10^6$ T cells.

In another embodiment, mitochondrially-enriched genetically engineered T cells are produced by the method of obtaining hematopoietic stem cells from a subject afflicted with a disease or disorder or a donor; obtaining exogenous mitochondria from a donor; producing mitochondrially-enriched hematopoietic stem cells under conditions allowing the exogenous mitochondria to enter the hematopoietic stem cells; differentiating the mitochondrially-enriched hematopoietic stem cells into mitochondrially-enriched T cells; and producing mitochondrially-enriched genetically engineered T cells by introducing a nucleic acid encoding a chimeric T cell receptor (TCR) or chimeric antigen receptor (CAR) into the mitochondrially-enriched T cells, wherein the exogenous mitochondrial content of the mitochondrially-enriched genetically engineered T cells is detectably higher than the mitochondrial content of the hematopoietic stem cells. In certain embodiments, the conditions for allowing the exogenous mitochondria to enter the hematopoietic stem cells is by contacting the hematopoietic stem cells with the exogenous mitochondria at a ratio of about 0.088-176 mU citrate synthase (CS) activity per $10^6$ hematopoietic stem cells.

In a further embodiment, the mitochondrially-enriched genetically engineered T cells are produced by the method of obtaining T cells from a subject afflicted with a disease or disorder or a donor; producing genetically engineered T cells by introducing a nucleic acid encoding a chimeric T cell receptor (TCR) or chimeric antigen receptor (CAR) into the T cells, obtaining exogenous mitochondria; producing mitochondrially-enriched genetically engineered T cells under conditions allowing the exogenous mitochondria to enter the genetically engineered T cells; wherein the mitochondrial content of the mitochondrially-enriched genetically engineered T cells is detectably higher than the mitochondrial content of the T cells. In certain aspects, the conditions allowing the exogenous mitochondria to enter the T cells includes contacting the T cells with the exogenous mitochondria at a ratio of about 0.088-176 mU citrate synthase (CS) activity per $10^6$ T cells.

According to some embodiments, the term "mitochondrial content" refers to functional and non-functional mitochondrial content. According to some embodiments, the term "mitochondrial content" refers to functional mitochondrial content.

The terms "T cells" and "T lymphocytes" are used interchangeably herein. T cell is specific type of lymphocyte that has an important role in controlling and shaping the immune response by providing a variety of immune-related functions. T cells can be distinguished from other lymphocytes by the presence of a T-cell receptor (TCR) on the cell surface. The term "T cells" as used herein includes cytotoxic T cells, T helper cells, regulatory T cells and natural killer T cells (NKT). According to some embodiments, the T cells are T cells precursors. According to other embodiments, the T cells are mature T cells. According to some embodiments, the T cells are fully differentiated T cells. In the methods of the invention, the T cells obtained from a subject afflicted with a disease or disorder or a donor are not actively altered or modified (e.g., reduction of mtDNA or mitochondrial function) prior to enrichment with exogenous mitochondria. More specifically, mitochondrial function and/or mitochondria DNA in the T cells is not actively altered or modified prior to contacting with exogenous mitochondria.

According to some embodiments, the T cells are genetically-engineered T cells. According to further embodiments, the genetically engineered T cells are selected from T-cell receptor (TCR)-transduced T cells and chimeric antigen receptor (CAR)-transduced T cells. Each possibility represents a separate embodiment of the present invention. According to specific embodiments, the genetically engineered T cells are CAR-T cells.

In some embodiments, the genetically engineered T cells are autologous to the subject. In some embodiments, the genetically engineered T cells are allogeneic to the subject. In specific embodiments, the allogeneic T cells are obtained from a donor which is at least partly HLA-matched with the subject. In certain embodiments, when the genetically engineered T cells are allogeneic to the subject, the method described above further comprises a step of administering to the subject an agent which prevents, delays, minimizes or abolishes an adverse immunogenic reaction between the subject and the mitochondrially-enriched human stem cells. Each possibility represents a separate embodiment of the present invention. In certain embodiments, the adverse immunogenic reaction is a graft-versus-host disease (GvHD).

The term "T cells are autologous to the subject" as used herein refers to being the subject's own cells. The term "T cells are allogeneic to the subject" as used herein refers to cells from a different donor individual.

The term "CAR-transduced T cells" and the term "CAR-T cells" are used interchangeably herein and refer to T cells that have been genetically modified to express chimeric antigen receptors (CARs) targeting a specific antigen. According to particular embodiments, the antigen presents on the surface of cancer cells. According to some embodiments, the cancer cells are hematological cancer cells. According to some embodiments, the CAR-T cells express CARs targeting an antigen selected from but not limited to CD19, CD30, CD33, CD123, FLT3 and BCMA.

As known to one of skill in the art, CAR-T cells are isolated from a subject and undergo ex vivo genetic manipulation using either lentiviral or retroviral vectors or non-viral gene transfer systems, to express the engineered CARs specific for particular tumor targets. These reprogrammed CAR-T cells are then expanded, selected if necessary, and infused into the subject after they have received an immunosuppressive preparative regimen. According to the principles of the present invention, the ex vivo genetic manipulation of the isolated T cells can be performed before or after the process of mitochondrial enrichment.

After transplantation, the CAR-T cells undergo antigen engagement and amplify in the peripheral blood, from where they travel to tumor sites and identify and kill tumor cells expressing the corresponding antigen. This can trigger extensive proliferation of CAR-T cells and the release of tumor antigens, which activate the subject's immune system to recruit non-CAR-T immune cells, thus eliciting further antitumor responses in a process known as cross-priming from epitope spreading.

When the number of CAR-T cells drops to undetectable levels after transplantation, disease relapse is frequently observed. It is now suggested that enriching CAR-T cells with exogenous mitochondria can enhance CAR-T cell survival and activity in vivo, thereby extending and amplifying the therapeutic effect of the cells.

The term "TCR-transduced T cells" and the term "TCR-T cells" are used interchangeably herein and refer to T cells that have been genetically modified to express T-cell receptors (TCRs). Unlike CAR-T cells that recognize proteins expressed on the surface, T cell Receptors (TCRs) can recognize tumor-specific proteins on the inside of cells. When tumor-specific proteins are broken into fragments, they show up on the cell surface with another protein called major histocompatibility complex, or MHC. TCRs are engineered to recognize a tumor-specific protein fragment/MHC combination.

According to some embodiments, the genetically-engineered T cells are derived from a mammalian subject, preferably a human subject.

According to some embodiments, the T cells of the invention are T cells having a lower mitochondrial membrane potential compared to corresponding T cells.

As used herein the term "mitochondrially-enriched genetically engineered T cells" refers to a T cell that has been genetically engineered (i.e. nucleic acid encoding a TCR or CAR was introduced into the cell) and had exogenous mitochondria inserted.

As used herein the term, "mitochondrially-enriched T cells" refers T cells with exogenous mitochondria inserted.

As used herein the term, "genetically engineered T cells" is T cell that has been genetically engineered (i.e. nucleic acid encoding a TCR or CAR was introduced into the cell).

As used herein the term, "mitochondrially-enriched hematopoietic stem cells" is a hematopoietic stem cell with exogenous mitochondria inserted.

As used herein, the term "stem cells" generally refers to any mammalian stem cells. Stem cells are undifferentiated cells that can differentiate into other types of cells and can divide to produce more of the same type of stem cells. Stem cells can be either totipotent or pluripotent.

As used herein, the term "human stem cells" generally refers to all stem cells naturally found in humans, and to all stem cells produced or derived ex vivo and are compatible with humans. A "progenitor cell", like a stem cell, has a tendency to differentiate into a specific type of cell, but is already more specific than a stem cell and is pushed to differentiate into its "target" cell. The most important difference between stem cells and progenitor cells is that stem cells can replicate indefinitely, whereas progenitor cells can divide only a limited number of times. The term "human stem cells" as used herein further includes "progenitor cells" and "non-fully differentiated stem cells".

In certain embodiments, the stem cells are pluripotent stem cells (PSC). In other embodiments, the PSCs are non-embryonic stem cells. According to some embodiments, embryonic stem cells are explicitly excluded from the scope of the invention. In some embodiments, the stem cells are induced PSCs (iPSCs). In certain embodiments, the stem cells are embryonic stem cells. In certain embodiments, the stem cells are derived from bone-marrow cells. In particular embodiments, the stem cells are CD34+ cells. In particular embodiments, the stem cells are mesenchymal stem cells. In other embodiments, the stem cells are derived from adipose tissue. In yet other embodiments, the stem cells are derived from blood. In further embodiments, the stem cells are derived from umbilical cord blood. In further embodiments the stem cells are derived from oral mucosa. In specific embodiments, the stem cells obtained from a subject afflicted with a disease of disorder or from a healthy subject are bone marrow cells or bone marrow-derived stem cells As used herein the term "pluripotent stem cells (PSCs)" refers to cells that can propagate indefinitely, as well as give rise to a plurality of cell types in the body. Totipotent stem cells are cells that can give rise to every other cell type in the body. Embryonic stem cells (ESCs) are totipotent stem cells and induced pluripotent stem cells (iPSCs) are pluripotent stem cells.

As used herein the term "induced pluripotent stem cells (iPSCs)" refers to a type of pluripotent stem cell that can be generated from human adult somatic cells. Some non-limiting examples of somatic cells from which iPSC can be generated herein include fibroblast cells, endothelial cells, capillary blood cells, keratinocytes, myeloid cells epithelial cells.

As used herein the term "embryonic stem cells (ESC)" refers to a type of totipotent stem cell derived from the inner cell mass of a blastocyst.

As used herein the term "bone marrow cells" generally refers to all human cells naturally found in the bone marrow of humans, and to all cell populations naturally found in the bone marrow of humans. The term "bone marrow stem cells" and "bone marrow-derived stem cells" refer to the stem cell population derived from the bone marrow.

In some embodiments, the autologous or allogeneic human stem cells are pluripotent stem cells (PSCs) or induced pluripotent stem cells (iPSCs). In further embodiments, the autologous or allogeneic human stem cells are mesenchymal stem cells.

According to several embodiments, the human stem cells are derived from adipose tissue, oral mucosa, blood, umbilical cord blood or bone marrow. Each possibility represents a separate embodiment of the present invention. In specific embodiments, the human stem cells are derived from bone marrow.

In certain embodiments, the bone-marrow derived stem cells include myelopoietic cells. The term "myelopoietic cells" as used herein refers to cells involved in myelopoiesis, e.g. in the production of bone-marrow and of all cells that arise from it, namely, all blood cells.

In certain embodiments, the bone-marrow derived stem cells include erythropoietic cells. The term "erythropoietic cells" as used herein refers to cells involved in erythropoiesis, e.g. in the production of red blood cells (erythrocytes).

In certain embodiments, the bone-marrow derived stem cells include multi-potential hematopoietic stem cells (HSCs). The term "multi-potential hematopoietic stem cells" or "hemocytoblasts" as used herein refers to the stem cells that give rise to all the other blood cells through the process of hematopoiesis.

In certain embodiments, the bone-marrow derived stem cells comprise common myeloid progenitor cells, common lymphoid progenitor cells, or any combination thereof. In certain embodiments, the bone-marrow derived stem cells comprise mesenchymal stem cells. The term "common myeloid progenitor" as used herein refers to the cells that generate myeloid cells. The term "common lymphoid progenitor" as used herein refers to the cells that generate lymphocytes.

In certain embodiments, the bone-marrow derived stem cells further comprise megakaryocytes, erythrocytes, mast cells, myoblasts, basophils, neutrophils, eosinophils, monocytes, macrophages, natural killer (NK) cells, small lymphocytes, T lymphocytes, B lymphocytes, plasma cells, reticular cells, or any combination thereof. Each possibility represents a separate embodiment of the invention.

In certain embodiments, the bone-marrow derived stem cells include mesenchymal stem cells. The term "mesenchymal stem cells" as used herein refers to multipotent stromal cells that can differentiate into a variety of cell types, including osteoblasts, chondrocytes, myocytes and adipocytes.

In certain embodiments, the bone-marrow derived stem cells include myelopoietic cells. In certain embodiments, the bone-marrow derived stem cells consist of erythropoietic cells. In certain embodiments, the bone-marrow derived stem cells include multi-potential hematopoietic stem cells (HSCs). In certain embodiments, the bone-marrow derived stem cells include common myeloid progenitor cells, common lymphoid progenitor cells, or any combination thereof. In certain embodiments, the bone-marrow derived stem cells include megakaryocytes, erythrocytes, mast cells, myoblasts, basophils, neutrophils, eosinophils, monocytes, macrophages, natural killer (NK) cells, small lymphocytes, T lymphocytes, B lymphocytes, plasma cells, reticular cells, or any combination thereof. In certain embodiments, the bone-marrow derived stem cells consist of mesenchymal stem cells. In certain embodiments, the stem cells include a plurality of human bone marrow stem cells obtained from peripheral blood.

Hematopoietic stem cells (HSCs) are the stem cells that give rise to other blood cells. This process is called hematopoiesis. Hematopoietic stem cells give rise to different types of blood cells, in lines called myeloid and lymphoid. Myeloid and lymphoid lineages both are involved in dendritic cell formation. Myeloid cells include monocytes, macrophages, neutrophils, basophils, eosinophils, erythrocytes, and megakaryocytes to platelets. Lymphoid cells include T cells, B cells, and natural killer cells.

Hematopoietic progenitor cell antigen CD34, also known as CD34 antigen, is a protein that in humans is encoded by the CD34 gene. CD34 is a cluster of differentiation in a cell surface glycoprotein and functions as a cell-cell adhesion factor. In certain embodiments, the bone-marrow stem cells express the bone-marrow progenitor cell antigen CD34 (are CD34+). In certain embodiments, the bone marrow stem cells do not express CD34. In certain embodiments, the bone marrow stem cells present the bone-marrow progenitor cell antigen CD34 on their external membrane. In certain embodiments the CD34+ cells are from umbilical cord blood. As used herein the term "CD34+ cells" refers to hematopoietic stem cells characterized as being CD34 positive, regardless of their origin. In certain embodiments, the CD34+ cells are obtained from the bone marrow, from bone marrow cells mobilized to the blood, or obtained from umbilical cord blood.

In certain embodiments, the stem cells, including hematopoietic stem cells, are obtained from the peripheral blood of the subject afflicted with a disease or disorder. In certain embodiments, the stem cells are obtained from the peripheral blood of a healthy. The term "peripheral blood" as used herein refers to blood circulating in the blood system.

As used herein, the term "autologous cells" or "cells that are autologous", refers to being the subject's own cells. The term "autologous mitochondria", refers to mitochondria obtained from the subject's own cells or from maternally related cells. The terms "allogeneic cells" or "allogeneic mitochondria", refer to cells or mitochondria being from a different donor individual.

The term "syngeneic" as used herein and in the claims refers to genetic identity or genetic near-identity sufficient to allow grafting among individuals without rejection. The term "syngeneic" in the context of mitochondria may be used interchangeably with the term "autologous mitochondria" meaning of the same maternal bloodline. Cells enriched with allogeneic mitochondria means that the exogenous mitochondria and the endogenous mitochondria are substantially genetically different, while cells enriched with syngeneic mitochondria means that the exogenous mitochondria and the endogenous mitochondria are genetically identical or near-identical, as the exogenous mitochondria are derived from maternally genetically related cells.

The terms "disease" and "disorder" are meant to refer to any affliction that are not considered normal or that are different from a physiological state. Disease and disorders can affect virtually any organ, tissue, or function is the body. Non limiting examples of diseases and condition include cancer, muscle diseases and disorders, glycogen-storage diseases and disorders, vascular endothelium disorder or diseases, brain disorder or brain disease, placental disorder or placental disease, thymus disorder or thymus disease, autoimmune diseases, renal disease or disorder, pancreas disorder or pancreas disease, prostate disorder or prostate disease, kidney disorder or kidney disease, blood disorder or blood disease, heart disease or heart disorder, skin disorder or skin disease, immune and inflammatory diseases and disorders, bone disease or bone disorder, gastro-intestinal disease or gastro-intestinal disorder, and eye disease or eye disorder.

As used herein the term "a subject afflicted with a disease or disorder" or "a subject having a disease or disorder" refers to a human subject experiencing debilitating effects caused by certain conditions. The disorder may refer to cancer, age related disorders, renal disease, pancreatic diseases, liver diseases, muscle disorders, brain disease, primary mitochondrial diseases or secondary mitochondrial disease, as well as other disease or disorders.

As used herein the term "donor" refers to a donor providing the exogenous cells or mitochondria. In some embodiments, the donor is not suffering from a disease or disorder or is not suffering from the same disease of disorder which the subject is afflicted. In certain embodiments, the donor is the subject and the cells and/or mitochondria are autologous.

The term "exogenous" or "isolated exogenous" with regard to mitochondria refers to mitochondria that are from a source which is external to the recipient cell. For example, in some embodiments, exogenous mitochondria are derived or isolated from a donor cell which is different than the donor of the recipient cell. In some embodiments, the exogenous mitochondria are derived from or isolated from a donor cell from the same subject as the recipient cell. For example, exogenous mitochondria may be purified, isolated or obtained from a donor cell and thereafter introduced into a recipient cell from the same subject as the donor cell or a different donor, making the exogenous mitochondria autologous and allogeneic, respectively. In certain embodiments, the exogenous mitochondria is whole mitochondria.

As used herein, the terms "isolated" and "partially purified" in the context of mitochondria includes exogenous mitochondria that are purified, or at least partially, from other cellular components. The total amount of mitochondrial proteins in an exogenous isolated or partially purified mitochondria is between 10%-90% of the total amount of cellular proteins within the sample.

In certain embodiments, the exogenous mitochondria constitute at least 1% of the total mitochondria content in the mitochondrially-enriched cells. In certain embodiments, the exogenous mitochondria constitute at least 3% of the total mitochondria content in the mitochondrially-enriched cells. In certain embodiments, the exogenous mitochondria constitute at least 10% of the total mitochondria content in the mitochondrially-enriched T cells. In some embodiments, the exogenous mitochondria constitute at least about 1%, 3%, 5%, 10%, 15%, 20%, 25% or 30% of the total mitochondria content in the mitochondrially-enriched T cells. In certain embodiments, the total amount of mitochondrial proteins in the exogenous mitochondria, is between 10%-80%, 20-80%, 40-70%, 20-40%, or 20-30% of the total amount of cellular proteins. Each possibility represents a separate embodiment of the present invention. In certain embodiments, the total amount of mitochondrial proteins in the exogenous mito- chondria, is between 10%-80% of the total amount of cellular proteins within the sample. In certain embodiments, the total amount of mitochondrial proteins in the exogenous mitochondria, is between 10%-80% of the combined weight of the mitochondria and other sub-cellular fractions. In other embodiments, the total amount of mitochondrial proteins in the exogenous mitochondria, is above 80% of the combined weight of the mitochondria and other sub-cellular fractions.

In certain embodiments, the exogenous mitochondria are obtained from a human cell or a human tissue. In certain embodiments, the cells are selected from the group consist- ing of placenta, placental cells grown in culture, or blood cells. In some embodiments, the mitochondria are obtained from human stem cells. In some embodiments, the human cell is a human somatic cell. In some embodiments, the human cell are cells grown in culture.

In certain embodiments, the methods and pharmaceutical compositions provided by the present invention further comprise a step of administering to the donor of the mito- chondria an agent which promotes mitochondrial biogen- esis. The term "mitochondrial biogenesis" as used herein refers to the growth and division of mitochondria. In certain embodiments, the agent which promotes mitochondrial bio- genesis is erythropoietin (EPO) or a salt thereof. In certain embodiments, the agent is selected from the group consist- ing of recombinant human erythropoietin and isolated human erythropoietin.

The term "endogenous" with regard to mitochondria refers to mitochondria that is being made/expressed/pro- duced by a cell and is not introduced from an external source into the cell. In some embodiments, endogenous mitochon- dria contain proteins and/or other molecules which are encoded by the genome of the cell. In some embodiments, the term "endogenous mitochondria" is equivalent to the term "host mitochondria".

According to the principles of the present invention, exogenous human mitochondria are introduced into cells thus enriching these cells with exogenous mitochondria. It should be understood that such enrichment changes the mitochondrial content of the cells: while naive human cells substantially have one population of host/autologous mito- chondria, cells enriched with exogenous mitochondria that is not autologous mitochondria substantially have two popu- lations of mitochondria, a first population of host/autolo- gous/endogenous mitochondria and another population of the introduced mitochondria (i.e., the exogenous mitochon- dria). Thus, the term "enriched" relates to the state of the cells after receiving/incorporation exogenous mitochondria. In certain embodiments, the exogenous mitochondria is autologous mitochondria. Where the exogenous mitochon- dria is autologous mitochondria there is only one population of mitochondria and enriched refers to total mitochondria content. Determining the number and/or ratio between the two populations of mitochondria is straightforward, as the two populations may differ in several aspects e.g. in their mitochondrial DNA. For example, human cells which com- prise at least 1% exogenous mitochondria of the total mitochondria content, are considered comprising host/au- tologous/endogenous mitochondria and exogenous mito- chondria in a ratio of 99:1. For example, "3% of the total mitochondria" means that after enrichment the original (endogenous) mitochondrial content is 97% of the total mitochondria content and the introduced (exogenous) mito- chondria is 3% of the total mitochondria content—this is equivalent to (3/97=) 3.1% enrichment. Another example— "33% of the total mitochondria" means that after enrich- ment, the original (endogenous) mitochondrial content is 67% of the total mitochondria content and the introduced (exogenous) mitochondria is 33% of the total mitochondria content—this is equivalent to (33/67=) 49.2% enrichment.

In some embodiments, the identification/discrimination of endogenous mitochondria from exogenous mitochondria, after the latter have been introduced into the cell, can be performed by various means, including, for example, but not limited to: identifying differences in mtDNA sequences, for example different haplotypes, between the endogenous mitochondria and exogenous mitochondria, identifying spe- cific mitochondrial proteins originating from of the source tissue of the exogenous mitochondria, such as, for example, cytochrome p450 cholesterol side chain cleavage (P450SCC) from placenta, UCP1 from brown adipose tis- sue, and the like, or any combination thereof.

Heteroplasmy is the presence of more than one type of mitochondrial DNA within a cell or individual. The hetero- plasmy level is the proportion of mutant mtDNA molecules vs. wild type/functional mtDNA molecules and is an impor- tant factor in considering the severity of mitochondrial diseases. While lower levels of heteroplasmy (sufficient amount of mitochondria are functional) are associated with a healthy phenotype, higher levels of heteroplasmy (insuf- ficient amount of mitochondria are functional) are associated with pathologies. In certain embodiments, the heteroplasmy level of the enriched cells, such as mitochondrially-enriched genetically engineered T cells, is at least 1%, 3%, 5%, 15%, 20%, 25%, or 30% lower than the heteroplasmy level of the cells obtained or derived from the subject or donor.

As used herein the term "contacting" refers to bringing the mitochondria and cells (for example, T cells and geneti- cally engineered T cells) into sufficient proximity to promote entry of the exogenous mitochondria into the cells. The term introducing or inserting mitochondria into the cells (for example, T cells and genetically engineered T cells) is used interchangeably with the term contacting.

The phrase "conditions allowing the exogenous mito- chondria to enter the T cells" and "conditions allowing the exogenous mitochondria to enter the genetically engineered T cells" as used herein generally refers to parameters such as time, temperature, centrifugation, culture medium and proximity between the mitochondria and the recipient cells. For example, human cells and human cell lines are routinely incubated in liquid medium, and kept in sterile environ- ments, such as in tissue culture incubators, at 37° C. and 5% $CO_2$ atmosphere. According to alternative embodiments disclosed and exemplified herein the cells may be incubated at room temperature in saline supplemented with human serum albumin.

In certain embodiments, the cells are incubated with the exogenous mitochondria for a time ranging from 0.5 to 30 hours, at a temperature ranging from about 16 to 37° C. In certain embodiments, the cells are incubated with the exog- enous mitochondria for a time ranging from about 1 to 30 or from about 5 to 25 hours. In specific embodiments, incuba- tion is for about 20 to 30 hours. In some embodiments, incubation is for at least about 1, 5, 10, 15, 20, 21, 22, 23 or 24. In other embodiments, incubation is up to 5, 10, 15, 20 or 30 hours. In specific embodiments, incubation is for 24 hours. In certain embodiments, incubation is until the mitochondrial content in the cells is increased in average by 1% to 45% compared to their initial mitochondrial content.

In some embodiments, incubation is at room temperature (16° C. to 30° C.). In other embodiments, incubation is at 37° C. In some embodiments, incubation is in a 5% $CO_2$ atmosphere. In other embodiments, incubation does not include added $CO_2$ above the level found in air.

In yet further embodiments, the incubation is performed in culture medium supplemented with human serum albumin (HSA). In additional embodiments, the incubation is performed in saline supplemented with HSA. According to certain exemplary embodiments, the conditions allowing the exogenous mitochondria to enter the human stem cells thereby enriching said human stem cells with said human exogenous mitochondria include incubation at room temperature in saline supplemented with 4.5% human serum albumin.

In certain embodiments, the incubation is performed at 37° C. In certain embodiments, the incubation is performed for at least 6 hours. In certain embodiments, the incubation is performed for at least 12 hours. In certain embodiments, the incubation is performed for 12 to 24 hours.

As used herein, the term "enriching" refers to any action designed to increase the mitochondrial content, e.g. the number of intact mitochondria, or the functionality of mitochondria of a mammalian cell. In particular, genetically engineered T cells enriched with exogenous mitochondria will show enhanced function compared to the same T cells prior to enrichment.

The terms "enriching" and "enrichment" as used herein refer to any action performed ex vivo, which increases the mitochondrial content, e.g. the number of intact, functional, or healthy mitochondria, of a human cell. According to the principles of the present invention, exogenous mitochondria are introduced into human T cells, thus enriching these cells with exogenous mitochondria. According to some embodiments, the exogenous mitochondria constitute above 1%, above 2%, above 3%, above 4%, above 5%, above 10%, above 15% or above 20% of the total mitochondria in the mitochondrially-enriched T-cells and mitochondrially-enriched genetically engineered T cells.

Citrate synthase (CS) is localized in the mitochondrial matrix, but is encoded by nuclear DNA. Citrate synthase is involved in the first step of the Krebs cycle, and is commonly used as a quantitative enzyme marker for the presence of intact mitochondria (Larsen S. et al., J. Physiol., 2012, Vol. 590 (14), pages 3349-3360; Cook G. A. et al., Biochim. Biophys. Acta., 1983, Vol. 763 (4), pages 356-367).

Mitochondrial dose can be expressed in terms of units of CS activity or mtDNA copy number of other quantifiable measurements of the amount of mitochondria as explained herein. A "unit of CS activity" is defined as the amount that enables conversion of one micromole substrate in 1 minute in 1 mL reaction volume.

In some embodiments, the enrichment of the cells (for example, T cells and genetically engineered T cells) with exogenous mitochondria includes introducing into the cells a dose of mitochondria of at least 0.044 up to 176 milliunits (mU) of citrate synthase (CS) activity per million cells; at least 0.088 up to 176 mU of CS activity per million cells; at least 0.2 up to 150 mU of CS activity per million cells; at least 0.4 up to 100 mU of CS activity per million cells; at least 0.6 up to 80 mU of CS activity per million cells; at least 0.7 up to 50 mU of CS activity per million cells; at least 0.8 up to 20 mU of CS activity per million cells; at least 0.88 up to 17.6 mU of CS activity per million cells; or at least 0.44 up to 17.6 mU of CS activity per million cells.

As used herein the term "mitochondrial content" refers to the amount of mitochondria within a cell, or to the average amount of mitochondria within a plurality of cells. The term "increased mitochondrial content" as used herein refers to a mitochondrial content which is detectably higher than the mitochondrial content of the cells prior to mitochondria enrichment.

In certain embodiments, the mitochondrial content of the cells enriched with exogenous mitochondria is detectably higher than the mitochondrial content of the naïve cells. According to various embodiments, the mitochondrial content of the mitochondrially-enriched genetically engineered T cells is at least 1%, at least 5%, at least 10%, at least 25%, at least 50%, at least 100%, at least 200% or more, higher than the mitochondrial content of the cells prior to mitochondria enrichment. In certain embodiments, the T cells or genetically engineered T cells are used fresh. In certain embodiments, the T cells or genetically engineered T cells, are frozen and thawed.

In certain embodiments, the mitochondrial content of the cells or mitochondrially-enriched genetically engineered T cells is determined by determining the content of citrate synthase. In certain embodiments, the mitochondrial content of the naïve cells or enriched cells is determined by determining the activity level of citrate synthase. In certain embodiments, the mitochondrial content of the naive cells or enriched cells correlates with the content of citrate synthase. In certain embodiments, the mitochondrial content of the naive cells or enriched cells correlates with the activity level of citrate synthase. CS activity can be measured by commercially available kits e.g., using the CS activity kit CS0720 (Sigma).

Mitochondrial DNA content may be measured by performing quantitative PCR of a mitochondrial gene prior and post mitochondrial enrichment, normalized to a nuclear gene.

In specific situations the same cells, prior to mitochondria enrichment, serve as controls to measure CS and ATP activity and determine enrichment level.

In certain embodiments, the term "detectably higher" as used herein refers to a statistically-significant increase between the normal and increased values. In certain embodiments, the term "detectably higher" as used herein refers to a non-pathological increase, i.e. to a level in which no pathological symptom associated with the substantially higher value becomes apparent. In certain embodiments, the term "increased" as used herein refers to a value which is 1.05 fold, 1.1 fold, 1.25 fold, 1.5 fold, 2 fold, 3 fold, 4 fold, 5 fold, 6 fold, 7 fold or higher than the corresponding value found in corresponding cells or corresponding mitochondria of a healthy subject or of a plurality of healthy subjects or in the cells (for example, T cells and genetically engineered T cells) prior to mitochondrial enrichment.

The term "increased mitochondrial DNA content" as used herein refers to the content of mitochondrial DNA which is detectably higher than the mitochondrial DNA content in cells prior to mitochondria enrichment. Mitochondrial content may be determined by measuring SDHA or COX1 content. "Normal mitochondrial DNA" in the context of the specification and claims refers to mitochondrial DNA not carrying/having a mutation or deletion that is known to be associated with a mitochondrial disease. The term "normal rate of oxygen ($O_2$) consumption" as used herein refers to the average $O_2$ consumption of cells from healthy individuals. The term "normal activity level of citrate synthase" as used herein refers to the average activity level of citrate synthase in cells from healthy individuals. The term "normal rate of adenosine triphosphate (ATP) production" as used herein refers to the average ATP production rate in cells from healthy individuals.

The extent of enrichment of the cells with exogenous mitochondria may be determined by functional and/or enzymatic assays, including but not limited to rate of oxygen ($O_2$) consumption, content or activity level of citrate synthase, rate of adenosine triphosphate (ATP) production. In the alternative the enrichment of the cells with exogenous mitochondria may be confirmed by the detection of mitochondrial DNA of the donor. According to some embodiments, the extent of enrichment of the cells with exogenous mitochondria may be determined by the level of change in heteroplasmy and/or by the copy number of mtDNA per cell.

TMRM (tetramethylrhodamine methyl ester) or the related TMRE (tetramethylrhodamine ethyl ester) are cell-permeant fluorogenic dyes commonly used to assess mitochondrial function in living cells, by identifying changes in mitochondrial membrane potential. According to some embodiments, the level of enrichment can be determined by staining with TMRE or TMRM.

According to some embodiments, the mitochondria comprises intact mitochondria, ruptured mitochondria and/or mitochondrial constituents selected from the group consisting of mitochondrial protein, mitochondrial nucleic acid, mitochondrial lipid and mitochondrial saccharide.

According to some embodiments, the intactness of a mitochondrial membrane may be determined by any method known in the art. In a non-limiting example, intactness of a mitochondrial membrane is measured using the tetramethylrhodamine methyl ester (TMRM) or the tetramethylrhodamine ethyl ester (TMRE) fluorescent probes. Each possibility represents a separate embodiment of the present invention. Mitochondria that were observed under a microscope and show TMRM or TMRE staining have an intact mitochondrial outer membrane. As used herein, the term "a mitochondrial membrane" refers to a mitochondrial membrane selected from the group consisting of the mitochondrial inner membrane, the mitochondrial outer membrane, and both.

In certain embodiments, the level of mitochondrial enrichment in the mitochondrially-enriched genetically engineered T cells is determined by sequencing at least a statistically-representative portion of total mitochondrial DNA in the cells and determining the relative levels of host/endogenous mitochondrial DNA and exogenous mitochondrial DNA. In certain embodiments, the level of mitochondrial enrichment in the mitochondrially-enriched genetically engineered T cells is determined by single nucleotide polymorphism (SNP) analysis. In certain embodiments, the largest mitochondrial population and/or the largest mitochondrial DNA population is the host/endogenous mitochondrial population and/or the host/endogenous mitochondrial DNA population; and/or the second-largest mitochondrial population and/or the second-largest mitochondrial DNA population is the exogenous mitochondrial population and/or the exogenous mitochondrial DNA population.

According to certain embodiments, the enrichment of the cells with exogenous mitochondria may be determined by conventional assays that are recognized in the art. In certain embodiments, the level of mitochondrial enrichment in the mitochondrially-enriched human genetically engineered T cells is determined by (i) the levels of host/endogenous mitochondrial DNA and exogenous mitochondrial DNA; (ii) the level of mitochondrial proteins selected from the group consisting of citrate synthase (CS), cytochrome C oxidase (COX1), succinate dehydrogenase complex flavoprotein subunit A (SDHA) and any combination thereof; (iii) the level of CS activity; or (iv) any combination of (i), (ii) and (iii). Methods for determining these various parameters are well known in the art.

In certain embodiments, the level of mitochondrial enrichment in the mitochondrially-enriched genetically engineered T cells is determined by at least one of: (i) the levels of host mitochondrial DNA and exogenous mitochondrial DNA; (ii) the level of citrate synthase activity; (iii) the level of succinate dehydrogenase complex flavoprotein subunit A (SDHA) or cytochrome Coxidase (COX1); (iv) the rate of oxygen ($O_2$) consumption; (v) the rate of adenosine triphosphate (ATP) production or (vi) any combination thereof. Each possibility represents a separate embodiment of the present invention. Methods for measuring these various parameters are well known in the art.

In some embodiments, enrichment of the cells with exogenous human mitochondria comprises washing the mitochondrially-enriched cells (for example mitochondrially-enriched genetically engineered T cells) after incubation of the cells with the exogenous human mitochondria. This step provides mitochondrially-enriched cells substantially devoid of cell debris or mitochondrial membrane remnants and mitochondria that did not enter the stem cells. In some embodiments, washing comprises centrifugation of the mitochondrially-enriched cells after incubation of the human cells with said exogenous human mitochondria. According to some embodiments, the methods produce mitochondrially-enriched cells that are separated from free mitochondria, i.e., mitochondria that did not enter the cells, or other cell debris and the pharmaceutical compositions contain mitochondrially-enriched cells that are separated from free mitochondria. According to some embodiments, the methods produce and the pharmaceutical compositions contain mitochondrially-enriched genetically engineered T cells that do not comprise a detectable amount of free mitochondria.

In certain embodiments, the method described above further includes concentrating the T cells or genetically engineered T cells, with the exogenous mitochondria before or during incubation and/or contacting. In certain embodiments, the method described above further includes centrifugation of T cells or genetically engineered T cells with exogenous mitochondria before, during or after incubation or contacting. In some embodiments, the methods described above in various embodiments thereof include a single centrifugation step before, during or after incubation of the cells with the exogenous mitochondria.

In certain embodiments, the centrifugation speed is 7,000 g or 8,000 g. According to further embodiments, the centrifugation is at a speed between 300 g-8000 g; 500 g-6000 g; 1000 g-5000 g: 2000 g-4000 g: 2500 g-8500 g; 3000 g-8000 g: 4000 g-8000 g; 5,000-10,000 g 7000 g-8000 g or above 2500 g. In some embodiments, centrifugation is performed for a time ranging from 2 minutes to 30 minutes; 3 minutes to 25 minutes; 5 minutes to 20 minutes; or 8 minutes to 15 minutes.

In some embodiments, centrifugation is performed in a temperature ranging from 2 to 6° C.; 4 to 37° C.; 4 to 10° C. or 16-30° C. In specific embodiments, centrifugation is performed at 4° C. In some embodiments, the methods described above in various embodiments thereof include a single centrifugation before, during or after incubation of the cells with the exogenous mitochondria, followed by resting the cells at a temperature lower than 30° C. In some embodiments, the conditions allowing the exogenous mitochondria to enter the human cells include a single centrifugation before, during or after incubation of the cells with the exogenous mitochondria, followed by resting the cells at a temperature ranging between 16 to 28° C.

In some embodiments, the methods generate and/or the pharmaceutical compositions contain mitochondrially-enriched genetically engineered T cells at a concentration of at least $10^5$ to $10^{10}$; $5\times10^5$ to $1.5\times10^7$; or $5\times10^5$ to $4\times10^7$ mitochondrially-enriched genetically engineered T cells per kilogram bodyweight of the subject. In some embodiments, the methods generate and/or pharmaceutical compositions contain mitochondrially-enriched genetically engineered T cells at a concentration of at least $10^6$ to $10^7$ mitochondrially-enriched genetically engineered T cells per kilogram bodyweight of the subject. In other embodiments, the methods generate and/or the pharmaceutical compositions contain mitochondrially enriched genetically engineered T cells at a concentration of at least $10^5$ or at least $10^6$ mitochondrially-enriched genetically engineered T cells per kilogram bodyweight of the subject. In some embodiments, the methods generate and/or the pharmaceutical compositions contain mitochondrially-enriched genetically engineered T cells at a concentration of a total of at least $5\times10^5$ up to $5\times10^9$ mitochondrially-enriched genetically engineered T cells. In some embodiments, the methods generate and/or the pharmaceutical compositions comprise mitochondrially-enriched genetically engineered T cells at a concentration of a total of at least $10^6$ up to $10^9$ mitochondrially-enriched genetically engineered T cells. In other embodiments, the methods generate and/or the pharmaceutical compositions comprises a total of at least $2\times10^6$ up to $5\times10^8$ mitochondrially-enriched genetically engineered T cells.

In certain embodiments, the T cells are fresh. In certain embodiments, the T cells are frozen and then thawed prior to incubation. In certain embodiments, the exogenous mitochondria is fresh. In certain embodiments, the exogenous mitochondria are frozen and then thawed prior to incubation. In certain embodiments, the mitochondrially-enriched genetically engineered T cells are fresh. In certain embodiments, the mitochondrially-enriched genetically engineered T cells are frozen and then thawed prior to administration.

In certain embodiments, the T cells then stored and used after thawing. In further embodiments, the exogenous mitochondria are frozen, then stored and thawed prior to use. In further embodiments the mitochondrially-enriched genetically engineered T cells are used without freezing and storage. In yet further embodiments, the mitochondrially-enriched genetically engineered T cells are used after freezing, storage and thawing. Methods suitable for freezing and thawing of cell preparations in order to preserve viability are well known in the art.

As used herein, the term "freeze-thaw cycle" refers to freezing of the exogenous mitochondria to a temperature below 0° C., maintaining the mitochondria in a temperature below 0° C. for a defined period of time and thawing the exogenous mitochondria to room temperature or body temperature or any temperature above 0° C. which enables treatment of the cells with the exogenous mitochondria. The term "room temperature", as used herein typically refers to a temperature of between 18° C. and 25° C. The term "body temperature", as used herein, refers to a temperature of between 35.5° C. and 37.5° C., preferably 37° C.

In another embodiment, the mitochondria that have undergone a freeze-thaw cycle were frozen at a temperature of −20° C. or lower; −4° C. or lower; or −70° C. or lower. According to another embodiment, freezing of the mitochondria is gradual. According to some embodiment, freezing of mitochondria is through flash-freezing. As used herein, the term "flash-freezing" refers to rapidly freezing the mitochondria by subjecting them to cryogenic temperatures.

In another embodiment, the mitochondria that underwent a freeze-thaw cycle were frozen for at least 30 minutes prior to thawing. According to another embodiment, the freeze-thaw cycle comprises freezing the exogenous mitochondria for at least 30, 60, 90, 120, 180, 210 minutes prior to thawing. Each possibility represents a separate embodiment of the present invention. In another embodiment, the mitochondria that have undergone a freeze-thaw cycle were frozen for at least 1, 2, 3, 4, 5, 6, 7, 8, 9, 10, 24, 48, 72, 96, or 120 hours prior to thawing. In another embodiment, the mitochondria that have undergone a freeze-thaw cycle were frozen for at least 4, 5, 6, 7, 30, 60, 120, 365 days prior to thawing. According to another embodiment, the freeze-thaw cycle comprises freezing the exogenous mitochondria for at least 1, 2, 3 weeks prior to thawing. According to another embodiment, the freeze-thaw cycle comprises freezing the exogenous mitochondria for at least 1, 2, 3, 4, 5, 6 months prior to thawing. Each possibility represents a separate embodiment of the present invention. According to another embodiment, the oxygen consumption of the exogenous mitochondria after the freeze-thaw cycle is equal or higher than the oxygen consumption of the exogenous mitochondria prior to the freeze-thaw cycle.

According to certain embodiment, thawing is at room temperature. In another embodiment, thawing is at body temperature. According to another embodiment, thawing is at a temperature which enables administering the mitochondria according to the methods of the invention. According to another embodiment, thawing is performed gradually.

In certain embodiments, the method described above further includes a preceding step of administering to the subject afflicted with a disease or disorder or the donor an agent which induces mobilization of bone-marrow cells to peripheral blood.

In certain embodiments, the agent which induces mobilization of bone-marrow cells/stem cells produced in the bone marrow to peripheral blood is selected from the group consisting of granulocyte-colony stimulating factor (G-CSF), granulocyte-macrophage colony-stimulating factor (GM-CSF), 1,1'-[1,4-Phenylenebis(methylene)]bis[1,4, 8,1 1-tetraazacyclotetradecane] (Plerixafor, CAS number 155148-31-5), CXCR4 inhibitors, a salt thereof, and any combination thereof. Each possibility represents a separate embodiment of the invention.

In certain embodiments, the method described above further includes isolating the cells from the peripheral blood of the subject afflicted with a disease or disorder and/or the donor. The term "isolating from the peripheral blood" as used herein refers to the isolation of T cells or hematopoietic stem cells from other constituents of the blood.

During apheresis, the blood of a subject or donor is passed through an apparatus that separates out one particular constituent and returns the remainder to the circulation. It is thus a medical procedure which is performed outside the body. In certain embodiments, the isolation is performed by apheresis.

In certain embodiments, the cells, are obtained from a subject afflicted with a disease or disorder or a donor, and the cells have (i) a normal rate of oxygen ($O_2$) consumption; (ii) a normal content or activity level of citrate synthase; (iii) a normal rate of adenosine triphosphate (ATP) production; or (iv) any combination of (i), (ii) and (iii).

In certain embodiments, the cells, which may be T cells, are obtained from a subject afflicted with a disease or disorder or a donor, and the T cells have (i) a decreased rate of oxygen ($O_2$) consumption; (ii) a decreased content or activity level of citrate synthase; (iii) a decreased rate of adenosine triphosphate (ATP) production; or (iv) any combination of (i), (ii) and (iii), as compared to a subject not afflicted with a disease or disorder.

In certain embodiments, the mitochondrially-enriched genetically engineered T cells have (i) an increased rate of oxygen ($O_2$) consumption; (ii) an increased content or activity level of citrate synthase; (iii) an increased rate of adenosine triphosphate (ATP) production; (iv) an increased mitochondrial DNA content or (v) any combination of (i), (ii), (iii) and (iv), as compared to corresponding T cells that have not undergone mitochondrial enrichment The term "increased rate of oxygen ($O_2$) consumption" as used herein refers to a rate of oxygen ($O_2$) consumption which is detectably higher than the rate of oxygen ($O_2$) consumption prior to mitochondria enrichment.

The term "increased content of at least one mitochondrial protein" as used herein refers to the content of either nuclear-encoded or mitochondrial-encoded mitochondrial proteins, e.g., CS, COX1 and SDHA, which is detectably higher than the content of said mitochondrial protein in the cells prior to mitochondrial enrichment.

The term "increased content or activity level of citrate synthase" as used herein refers to a content or activity level of citrate synthase which is detectably higher than the content value or activity level of citrate synthase in cells prior to mitochondrial enrichment.

The term "increased rate of adenosine triphosphate (ATP) production" as used herein refers to a rate of adenosine triphosphate (ATP) production which is detectably higher than the rate of adenosine triphosphate (ATP) production prior to mitochondria enrichment.

According to yet another aspect, the present invention provides a method for treating a disease selected from the group consisting of cancer, an infectious disease or an autoimmune disease, the method comprising administering a therapeutically effective amount of a pharmaceutical composition comprising a plurality of mitochondrially-enriched genetically engineered T cells to a subject in need thereof.

According to some embodiments, the disease is cancer. The term "cancer" refers to a group diseases characterized by abnormal and uncontrolled cell proliferation starting at one site (primary site) with the potential to invade and to spread to others sites (secondary sites, metastases) which differentiate cancer (malignant tumor) from benign tumor. Virtually all the organs can be affected, leading to more than 100 types of cancer that can affect humans. Cancers can result from many causes including genetic predisposition, viral infection, exposure to ionizing radiation, exposure environmental pollutant, tobacco and or alcohol use, obesity, poor diet, lack of physical activity or any combination thereof. As used herein, "neoplasm" or "tumor" including grammatical variations thereof, means new and abnormal growth of tissue, which may be benign or cancerous. In a related aspect, the neoplasm is indicative of a neoplastic disease or disorder, including but not limited, to various cancers. For example, such cancers can include prostate, pancreatic, biliary, colon, rectal, liver, kidney, lung, testicular, breast, ovarian, pancreatic, brain, and head and neck cancers, melanoma, sarcoma, multiple myeloma, leukemia, lymphoma, and the like.

Cancer that begins in blood-forming tissue, such as the bone marrow, or in the cells of the immune system are referred to as hematologic cancer, or blood cancer. Hematologic cancers affect the production and function of blood cells, and are classified in three main types: leukemia, lymphoma, and multiple myeloma.

As used herein, "leukemia" refers to a blood caused by the rapid production of abnormal white blood cells. Examples of leukemia include acute lymphoblastic leukemia (ALL), acute myeloid leukemia (AML), chronic lymphocytic leukemia (CLL), chronic myelogenous leukemia (CML), and hairy cell leukemia.

As used herein, "lymphoma" refers to a type of blood cancer that affects the lymphatic system. Examples of lymphoma include AIDS-related lymphoma, cutaneous T-cell lymphoma, Hodgkin's lymphoma, mycosis fungoides, non-Hodgkin lymphoma, primary central nervous system lymphoma, Sézary syndrome, cutaneous T-Cell lymphoma, and Waldenström macroglobulinemia.

As used herein, "myeloma" is a cancer of the plasma cells. Examples of myeloma include chronic myeloproliferative neoplasms, Langerhans cell histiocytosis, multiple myeloma, plasma cell neoplasm, myelodysplastic syndromes, and myelodysplastic/myeloproliferative neoplasms.

In some embodiments, the cancer is hematological cancer. In certain embodiments, the cancer include acute lymphoblastic leukemia (ALL), acute myeloid leukemia (AML), chronic lymphocytic leukemia (CLL), chronic myelogenous leukemia (CML), hairy cell leukemia, Hodgkin's lymphoma, non-Hodgkin's lymphoma or multiple myeloma.

In some aspects, administration can be in combination with one or more additional therapeutic agents. The phrases "combination therapy", "combined with" and the like refer to the use of more than one medication or treatment simultaneously to increase the response. The composition of the present invention might for example be used in combination with other drugs or treatment in use to treat cancer. Specifically, the administration of the composition of the present invention to a subject can be in combination with any anti-cancer therapies. Such therapies can be administered prior to, simultaneously with, or following administration of the composition of the present invention.

The term "anti-cancer therapy" or "anti-cancer treatment" as used herein is meant to refer to any treatment that can be used to treat cancer, such as surgery, radiotherapy, chemotherapy, immunotherapy, and checkpoint inhibitor therapy.

The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLES

Example 1

In one aspect, the invention provides the following method for treating a subject as described herein:

Enrich isolated T-cells with mitochondria as described herein where the mitochondria have been freeze/thawed using freeze/thaw cycles.

Introduce to the cells a nucleic acid polymer encoding a chimeric T cell receptor or a chimeric antigen receptors (CARs).

Administer the mitochondrial enriched cells to the subject.

Example 2

In one aspect, the invention provides the following method for treating a subject as described herein:

Introduce to isolated T cells, a nucleic acid polymer encoding a chimeric T cell receptor or a chimeric antigen receptors (CARs).

Enrich the cells with mitochondria.

Administer the enriched cells to the subject.

Example 3

Peripheral blood mononuclear cells (PBMCs) from a healthy human donor were thawed and cultured with interleukin 2. After two days of recovery, cells were activated using OKT3 (50 ng/ml) (i.e. day 0 of protocol).

For transduction with a retrovirus encoding the CD19-CAR with a CD28 costimulatory domain non-tissue culture plates were coated with retronectin overnight in room temperature on day 2. On day 3, virus was thawed, added to retronectin-coated plates, and spun for 2 hours at 32° C. Virus was then removed from plates and activated donor cells were plated ($0.5 \times 10^6$/ml), and placed in an incubator. As control, untransduced cells were plated on plates without a virus. Cells were grown in RPMI medium supplemented with 10% fetal bovine serum (FBS), and IL-2 (100 IU/ml) and media was changed every 2-3 days.

For mitochondrial enrichment, cryopreserved mitochondria isolated from placenta of a healthy individual (MNV-PLC) were thawed and added to the cells at 0.88 mU or 4.4 mU CS activity per $1 \times 10^6$ cells on either day 5 or day 10 of cell activation. Mitochondrially enriched cells, as well as non-enriched cells, were either centrifuged at 7000 g (A1) or 400 g (A2) for 5 minutes at 4° C. After centrifugation, cells were suspended in the same media (RPMI-10% FCS supplemented with 100 U/ml IL-2) and incubated at 37° C. for 22 hours. After 22 hr, cells were harvested, washed and resuspended in RPMI. Mitochondrial enrichment was verified by identifying the presence of the exogenous placental mitochondria in the cells by sequencing analysis. CAR-T cells which underwent the same procedure and were incubated for 22 hours at 37° C. without exogenous mitochondria served as control.

Figure 1B:
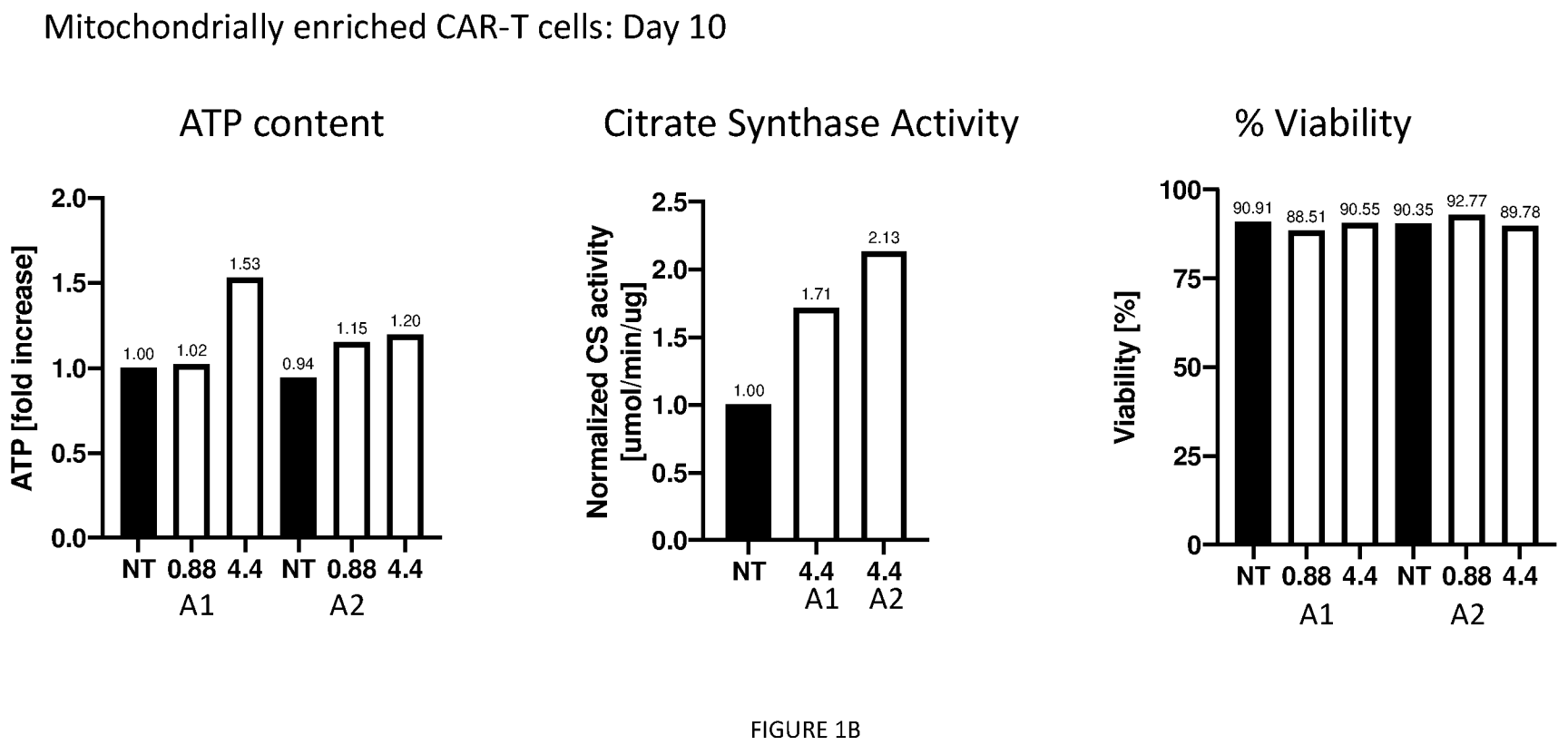
Figure 1C:
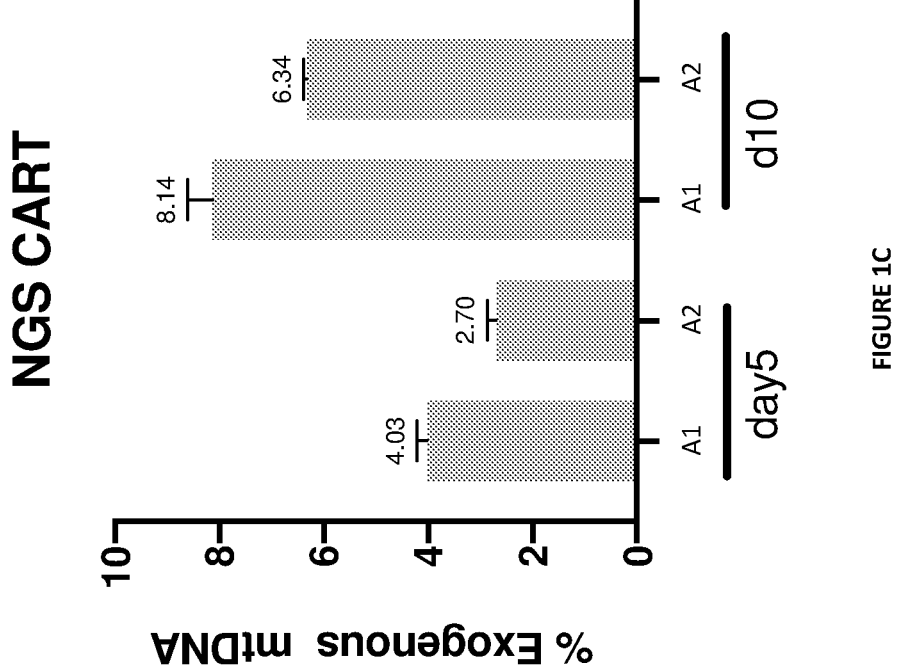
Figure 2:
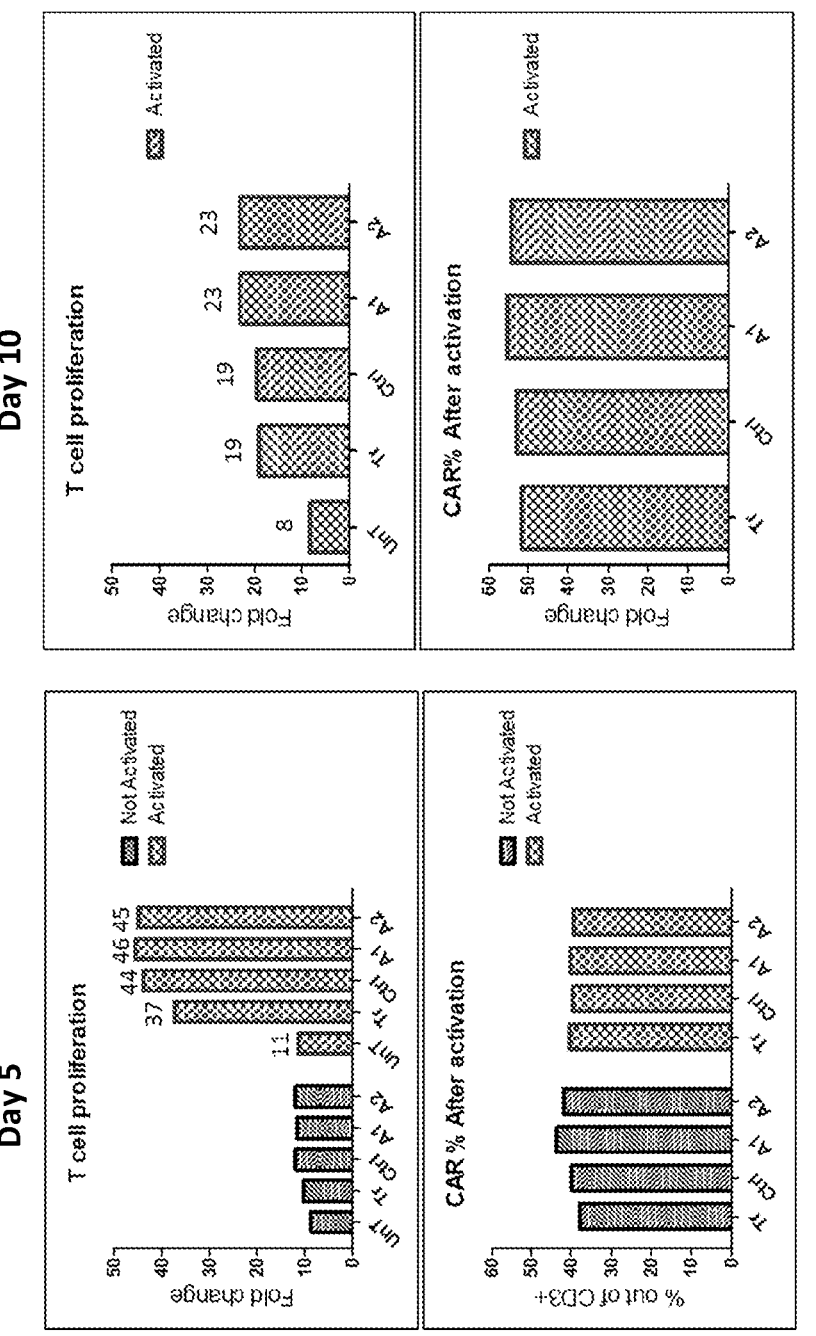
FIG. 2 shows proliferation of activated and non-activated T cells and % CAR-T after activation. A1: CAR-T cells enriched with 4.4 mU placental mitochondria at 7000 g; A2: CAR-T cells enriched with 4.4 mU placental mitochondria at 400 g; UnT: non transduced non-enriched cells; Tr: transduced cells that were not subjected to mitochondrial enrichment conditions; Ctrl: transduced cells subjected to mitochondrial enrichment conditions without introducing exogenous mitochondria to enrichment process.

Treatment of CAR-T cells with 4.4 mU or 0.88 mU of MNV-PLC resulted in mitochondrial enrichment as verified by sequence analysis. Mitochondrial enrichment of CAR-T cells was feasible on day 5 or day 10 from cell activation. Mitochondrial enrichment performed on day 5 resulted in 90.3-95.5% viability, 1.05-1.21-fold increase in ATP content compared to control cells and 1.7-2.6-fold increase in normalized CS activity compared to control cells. Mitochondrial enrichment performed on day 10 resulted in 88.5-92.7% viability, 1.02-1.53-fold increase in ATP content compared to control cells and 1.7-2.13-fold increase in normalized CS activity compared tp control cells. Control cells were transduced cells subjected to augmentation conditions without introducing exogenous mitochondria to the process. (FIG. 1B). Mitochondrial enrichment performed on day 10 had a 2-fold or 3-fold increase in exogenous mitochondria incorporation compared to mitochondrial enrichment performed on day 5 (8.14% vs. 4.03% in A1, and 6.34% vs. 2.7% in A2) (FIG. 1C). T-cell proliferative capacity and transduction efficacy were not impaired by mitochondrial enrichment (FIG. 2).

Although the invention has been described with reference to the above examples, it will be understood that modifications and variations are encompassed within the spirit and scope of the invention. Accordingly, the invention is limited only by the following claims.

What is claimed is:

1. A pharmaceutical composition comprising mitochondrially-enriched genetically engineered T cells and a pharmaceutically acceptable carrier, wherein the mitochondrially-enriched genetically engineered T cells are produced by a method comprising:

a) contacting T cells obtained from a subject afflicted with a disease or disorder or from a donor with exogenous mitochondria at a ratio of about 0.88-4.4 mU citrate synthase (CS) activity per $10^6$ T cells, and introducing a nucleic acid encoding a chimeric T cell receptor (TCR) or chimeric antigen receptor (CAR) into the T cells; or b) introducing a nucleic acid encoding a chimeric TCR or CAR into T cells obtained from a subject afflicted with a disease or disorder or from a donor, and contacting the T cells with exogenous mitochondria at a ratio of about 0.88-4.4 mU CS activity per $10^6$ T cells, wherein the mitochondrial content of the mitochondrially-enriched genetically engineered T cells is at least 1% higher than the mitochondrial content of the T cells prior to contacting the T cells with the exogenous mitochondria, and the method does not comprise reducing mtDNA content of the T cells prior to contacting the T cells with the exogenous mitochondria.

2. The pharmaceutical composition of claim 1, wherein the genetically engineered T cells and mitochondrially-enriched genetically engineered T cells are CAR-T cells.

3. The pharmaceutical composition of claim 1, wherein the genetically engineered T cells and mitochondrially-enriched genetically engineered T cells are TCR-T cells.

4. The pharmaceutical composition of claim 1, wherein the exogenous mitochondria are derived from a human cell.

5. The pharmaceutical composition of claim 4, wherein the human cell is selected from human placenta, human placental cells grown in culture, human blood cells, stem cells and somatic cells.

6. The pharmaceutical composition of claim 5, wherein the stem cells are selected from the group consisting of induced pluripotent stem cells, embryonic stem cells and pluripotent stem cells.

7. The pharmaceutical composition of claim 1, wherein the exogenous mitochondria are syngeneic or allogeneic.

8. The pharmaceutical composition of claim 1, wherein the exogenous mitochondria are autologous.

9. The pharmaceutical composition of claim 1, wherein the pharmaceutical composition comprises about $5 \times 10^5$ to about $5 \times 10^{10}$ mitochondrially-enriched genetically engineered T cells.

10. The pharmaceutical composition of claim 1, wherein the mitochondrially-enriched genetically-engineered T-cells have at least one of:

(a) an increased mitochondrial DNA content;

(b) an increased level of citrate synthetase (CS) activity;

(c) an increased content of at least one mitochondrial protein selected from SDHA and COX1;

(d) an increased rate of O2 consumption;

(e) an increased rate of ATP production; or (f) any combination thereof, relative to the corresponding level in the T-cells prior to mitochondrial enrichment.

11. The pharmaceutical composition of claim 1, wherein the exogenous mitochondria constitute at least 1% of the total mitochondria in the mitochondrially-enriched T cells or mitochondrially-enriched genetically engineered T-cells.

12. The pharmaceutical composition of claim 1, wherein the disease or disorder is cancer.

13. The pharmaceutical composition of claim 12, wherein the cancer is hematological cancer.

14. The pharmaceutical composition of claim 1, wherein the T cells are autologous or allogenic.

15. A method of treating a disease or disorder in a subject in need thereof comprising administering to the subject mitochondrially-enriched genetically engineered T cells, wherein the method further comprises the following steps for preparing the mitochondrially-enriched genetically engineered T cells:

a) contacting T cells obtained from a subject afflicted with a disease or disorder or from a donor with exogenous mitochondria at a ratio of about 0.88-4.4 mU citrate synthase (CS) activity per $10^6$ T cells, and introducing a nucleic acid encoding a chimeric T cell receptor (TCR) or chimeric antigen receptor (CAR) into the T cells; or b) introducing a nucleic acid encoding a chimeric TCR or CAR into T cells obtained from a subject afflicted with a disease or disorder or a from donor, and contacting the T cells with exogenous mitochondria at a ratio of about 0.88-4.4 mU CS activity per $10^6$ T cells, wherein the mitochondrial content of the mitochondrially-enriched genetically engineered T cells is at least 1% higher than the mitochondrial content of the T cells prior to contacting the T cells with the exogenous mitochondria, and the method does not comprise reducing mtDNA content of the T cells prior to contacting the T cells with the exogenous mitochondria.

16. The pharmaceutical composition of claim 1, wherein the method further comprises activating the T cells obtained from the subject prior to contacting with the exogenous mitochondria, and contacting the activated T cells with the exogenous mitochondria on day 10 following activation of the T cells.

17. The pharmaceutical composition of claim 1, wherein the ratio of CS activity per $10^6$ T cells is about 0.88 or about 4.4 mU.

18. A method of preparing mitochondrially-enriched genetically engineered T cells, comprising:

a) contacting T cells obtained from a subject afflicted with a disease or disorder or from a donor with exogenous mitochondria at a ratio of about 0.88-4.4 mU citrate synthase (CS) activity per $10^6$ T cells, and introducing a nucleic acid encoding a chimeric T cell receptor (TCR) or chimeric antigen receptor (CAR) into the T cells; or b) introducing a nucleic acid encoding a chimeric TCR or CAR into T cells obtained from a subject afflicted with a disease or disorder or from a donor, and contacting the T cells with exogenous mitochondria at a ratio of about 0.88-4.4 mU CS activity per $10^6$ T cells, wherein the mitochondrial content of the mitochondrially-enriched genetically engineered T cells is at least 1% higher than the mitochondrial content of the T cells prior to contacting the T cells with the exogenous mitochondria, and the method does not comprise reducing mtDNA content of the T cells prior to contacting the T cells with the exogenous mitochondria.

\* \* \* \* \*